United States Patent
Daley et al.

(10) Patent No.: US 12,402,963 B2
(45) Date of Patent: Sep. 2, 2025

(54) APPARATUS, SYSTEMS, AND METHODS TO FACILITATE INSTRUMENT VISUALIZATION

(71) Applicant: Auris Health, Inc., Redwood City, CA (US)

(72) Inventors: Devon Manuel Daley, San Mateo, CA (US); Zihan Chen, Union City, CA (US); Enrique Romo, Danville, CA (US)

(73) Assignee: Auris Health, Inc., Santa Clara, CA (US)

( * ) Notice: Subject to any disclaimer, the term of this patent is extended or adjusted under 35 U.S.C. 154(b) by 878 days.

(21) Appl. No.: 16/936,419

(22) Filed: Jul. 22, 2020

(65) Prior Publication Data
US 2021/0030497 A1    Feb. 4, 2021

Related U.S. Application Data

(60) Provisional application No. 62/881,346, filed on Jul. 31, 2019.

(51) Int. Cl.
*A61B 34/35*    (2016.01)
*A61B 18/00*    (2006.01)
*A61B 34/00*    (2016.01)
*G02B 6/02*    (2006.01)

(52) U.S. Cl.
CPC ............. *A61B 34/35* (2016.02); *A61B 34/76* (2016.02); *G02B 6/02076* (2013.01); *A61B 2018/00297* (2013.01); *A61B 2562/028* (2013.01)

(58) Field of Classification Search
CPC ................. A61B 34/76; A61B 2018/00297
See application file for complete search history.

(56) References Cited

U.S. PATENT DOCUMENTS

| | | | |
|---|---|---|---|
| 8,483,816 B1 * | 7/2013 | Payton | A61B 34/30 700/245 |
| 9,403,056 B2 * | 8/2016 | Weinberg | A63B 21/4045 |
| 9,582,096 B2 * | 2/2017 | Narita | G06F 3/0412 |
| 10,149,720 B2 * | 12/2018 | Romo | A61B 17/00234 |
| 10,219,874 B2 * | 3/2019 | Yu | A61M 25/0012 |
| 10,730,187 B2 * | 8/2020 | Larkin | A61B 1/0051 |
| 2005/0273254 A1 * | 12/2005 | Malchi | G01C 21/005 702/152 |
| 2008/0004603 A1 * | 1/2008 | Larkin | A61B 34/25 606/1 |
| 2008/0287805 A1 * | 11/2008 | Li | A61B 34/20 600/471 |
| 2009/0112469 A1 * | 4/2009 | Lapidot | G01C 23/00 701/469 |

(Continued)

*Primary Examiner* — Oommen Jacob
(74) *Attorney, Agent, or Firm* — Frost Brown Todd LLP

(57) ABSTRACT

Disclosed embodiments pertain to apparatus, systems, and method for facilitating instrument visualization and use in robotic medical devices. In some embodiments, for one or more instruments coupled to a robotic medical device, one or more corresponding instrument positions relative to a current field of view (FOV) of least one image sensor coupled to the robotic medical device may be obtained. Feedback, which may be haptic and/or visual, may be initiated for a selected instrument based on a position of the selected instrument relative to the current FOV.

19 Claims, 11 Drawing Sheets

(56) References Cited

U.S. PATENT DOCUMENTS

| | | | |
|---|---|---|---|
| 2009/0120696 A1* | 5/2009 | Hayakawa | G06F 3/045 |
| | | | 178/18.05 |
| 2010/0331856 A1 | 12/2010 | Carlson et al. | |
| 2012/0113030 A1* | 5/2012 | Park | H04M 1/72469 |
| | | | 345/173 |
| 2013/0211588 A1* | 8/2013 | Diolaiti | B25J 9/1689 |
| | | | 700/249 |
| 2013/0222339 A1* | 8/2013 | Koga | G06F 3/016 |
| | | | 345/174 |
| 2014/0276938 A1* | 9/2014 | Hsu | A61B 34/76 |
| | | | 606/130 |
| 2015/0230697 A1 | 8/2015 | Phee et al. | |
| 2016/0049217 A1* | 2/2016 | Tee | H01B 1/22 |
| | | | 73/862.627 |
| 2017/0165013 A1* | 6/2017 | Itkowitz | A61B 34/35 |
| 2017/0202624 A1* | 7/2017 | Atarot | G16H 40/63 |
| 2017/0215823 A1* | 8/2017 | Ivanov | A61B 6/545 |
| 2018/0228343 A1* | 8/2018 | Seeber | A61B 34/20 |
| 2018/0242941 A1* | 8/2018 | Grass | G06T 7/251 |
| 2020/0304753 A1* | 9/2020 | Venkataraman | A61B 1/00045 |

* cited by examiner

APPARATUS, SYSTEMS, AND METHODS TO FACILITATE INSTRUMENT VISUALIZATION

CROSS-REFERENCE TO RELATED APPLICATION

This application claims the benefit of and priority to U.S. Provisional Patent Application No. 62/881,346 entitled, "APPARATUS, SYSTEMS, AND METHODS TO FACILITATE INSTRUMENT VISUALIZATION," filed Jul. 31, 2019, which is assigned to the assignee hereof, and incorporated by reference in its entirety, herein.

FIELD

The subject matter disclosed herein relates to robotic medical systems, devices, and methods to facilitate instrument visualization.

BACKGROUND

Robotic medical systems are often used during minimally invasive or non-invasive medical procedures for imaging tissue, performing biopsies, surgery, and/or other medical procedures. In many instances, these medical procedures can be hampered because instruments associated with the robotic medical system may be outside the Field of View (FOV) of a camera used by the robotic medical system at some stage of the medical procedure. Because cameras on many robotic medical devices used for minimally invasive or non-invasive procedures typically have a limited FOV and/or limited maneuverability, an operator (e.g. a medical professional) may encounter situations where the instruments are out of the FOV relatively frequently. Moreover, the operator may find it difficult to determine a direction of movement for the instrument(s) and/or a movement distance in order to bring the instrument(s) into the FOV of the camera. The inability to see instruments and/or difficulty in determining how to bring instruments into the FOV of the camera can encumber professionals, impact safety, and lengthen procedure time thereby decreasing efficiency and increasing cost. In addition, keeping track of instruments and/or maintaining FOV can significantly increase operator cognitive load and detract focus from substantive procedures. Accordingly, some embodiments disclosed herein enhance safety and improve procedural efficiency, in part by facilitating instrument visualization and control during medical procedures.

SUMMARY

In some embodiments, a method on a robotic medical system may comprise: obtaining, for one or more instruments coupled to a robotic medical device, one or more corresponding instrument positions relative to a current field of view (FOV) of least one image sensor coupled to the robotic medical device; and initiating, for a selected instrument of the one or more instruments, generation of a corresponding feedback to a user, wherein the corresponding feedback is based on a position of the selected instrument relative to the current FOV. In some embodiments, to obtain the one or more corresponding instrument positions relative to the current FOV, the method may comprise: determining, based on a corresponding current pose associated with at least one image sensor coupled to a robotic medical device, the current FOV of the at least one image sensor; and determining the one or more corresponding instrument positions relative to the current FOV based on: one or more images captured by the at least one image sensor, or a control model for the robotic medical device, or sensor input from one or more sensors coupled to the robotic medical device, or a combination thereof.

In another aspect, a robotic medical device may comprise: at least one image sensor; one or more instruments; and a processor communicatively coupled to the at least one image sensor and the one or more instruments, wherein the processor is configured to: obtain, for the one or more instruments, one or more corresponding instrument positions relative to a current field of view (FOV) of the least one image sensor; and initiate, for a selected instrument of the one or more instruments, generation of a corresponding feedback to a user, wherein the corresponding feedback is based on a position of the selected instrument relative to the current FOV. In some embodiments, the robotic medical device may further comprise one or more sensors coupled to the processor, wherein to obtain the one or more corresponding instrument positions relative to the current field of view (FOV), the processor may be configured to: determine, based on a corresponding current pose associated with the at least one image sensor, the current FOV of the at least one image sensor; and determine, the one or more corresponding instrument positions relative to the current FOV based on: one or more images captured by the at least one image sensor, or a control model for the robotic medical device, or sensor input from the one or more sensors, or a combination thereof.

In a further aspect, a non-transitory computer-readable medium may comprise instructions to configure a processor on a robotic medical device to: obtain, for one or more instruments coupled to a robotic medical device, one or more corresponding instrument positions relative to a current field of view (FOV) of least one image sensor coupled to the robotic medical device; and initiate, for a selected instrument of the one or more instruments, generation of a corresponding feedback to a user, wherein the corresponding feedback is based on a position of the selected instrument relative to the current FOV. In some embodiments, to obtain the one or more corresponding instrument positions relative to the current field of view (FOV), the instructions may configure the processor to: determine, based on a corresponding current pose associated with at least one image sensor coupled to the robotic medical device, the current FOV of the at least one image sensor; and determine, the one or more corresponding instrument positions relative to the current FOV based on: one or more images captured by the at least one image sensor, or a control model for the robotic medical device, or sensor input from one or more sensors coupled to the robotic medical device, or a combination thereof.

In some embodiments, an apparatus may comprise: means for obtaining, for one or more instruments coupled to a robotic medical device, one or more corresponding instrument positions relative to a current field of view (FOV) of least one image sensing means coupled to the robotic medical device; and means for initiating, for a selected instrument of the one or more instruments, generation of a corresponding feedback to a user, wherein the corresponding feedback is based on a position of the selected instrument relative to the current FOV. In some embodiments, means for obtaining, the one or more corresponding instrument positions relative to the current FOV may comprise: means for determining, based on a corresponding current pose associated with the image sensing means, the current FOV of the image sensing means; and means for determining the one or more corresponding instrument positions relative to the current FOV based on: one or more images captured by the image sensing means, or a control model for the apparatus, or sensor means input from one or more sensor means, or a combination thereof.

BRIEF DESCRIPTION OF THE DRAWINGS

Embodiments of the invention will be described, by way of example only, with reference to the drawings.

Figure 1A:
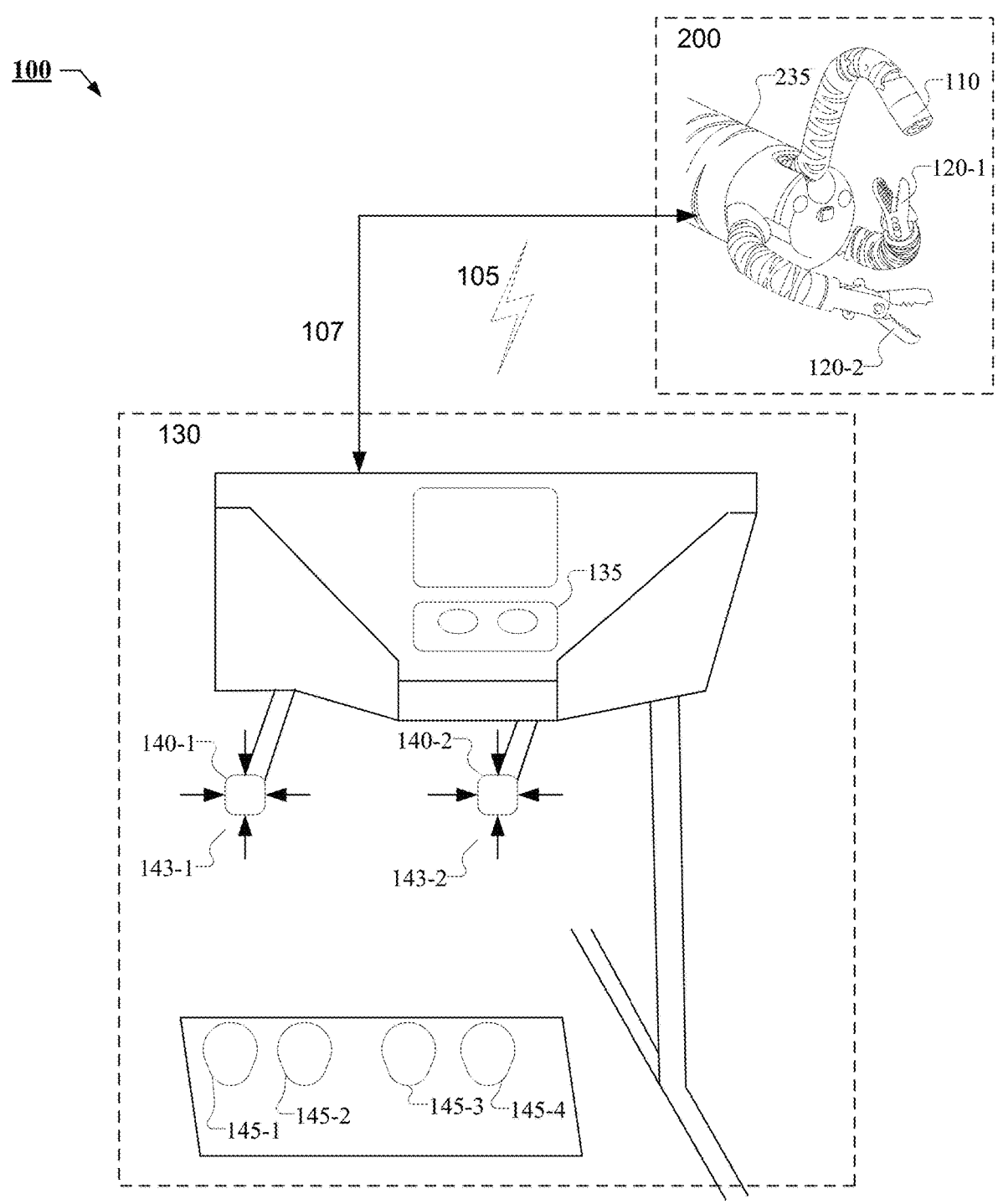
FIG. 1A shows an example diagram illustrating some features of a robotic medical system in accordance with certain embodiments disclosed herein.

Like reference numbers and symbols in the various figures indicate like elements, in accordance with certain example embodiments. In addition, multiple instances of an element may be indicated by following a first number for the element with a letter or with a hyphen and a second number. For example, multiple instances of an element 120 may be indicated as 120-1, 120-2, 120-3 etc. When referring to such an element using only the first number, any instance of the element is to be understood (e.g. element 120 in the previous example would refer to elements 120-1, 120-2, and/or 120-3).

DETAILED DESCRIPTION

Some disclosed embodiments pertain to robotically driven medical devices and systems and facilitate visualization of instruments during medical procedures such as endoscopy, laparoscopy, and/or endolumenal procedures. In some embodiments, a robotically driven device may comprise a user-controlled robotically driven flexible articulating main sheath (which may also be referred to as a "mother sheath"). One or more robotically driven image sensors and one or more robotically driven instruments may be coupled to a distal end of the main sheath. For example, in some embodiments, the one or more image sensors may be coupled to the distal end of a flexible articulating image sensor sub-arm and a proximal end of the image sensor sub-arm may be coupled to the distal end of the main-sheath. Further, in some embodiments, each instrument may be may be coupled to the distal end of a corresponding flexible articulating instrument sub-arm and a proximal end of the corresponding instrument sub-arm may be coupled to the distal end of the main-sheath. Thus, in some embodiments, the distal end of the main sheath may be coupled to the proximal end of a plurality of sub-arms, and the distal end of each sub-arm may coupled to at least one corresponding instrument and/or at least one image sensor. Each flexible articulating (image sensor and/or instrument) sub-arm may be retractable into the main sheath and housed in the main sheath when in a retracted state. The term "sub-arm," when used without a qualifier, may refer to any type of sub-arm (e.g. either image sensor sub-arm or instrument sub-arms).

In some embodiments, the main sheath and each sub-arm may be robot driven and operation and motion of the main sheath and each sub-arm may be individually controlled by an operator (e.g. a medical professional) through a user-interface. The selection (e.g. of the main sheath and/or one or more image sensors/image sensor-sub arms, and/or one or more instruments/instrument sub-arms), activation (e.g. turning on the image sensor(s)), deployment (e.g. extension and/or retraction of the main sheath and/or each sub-arm), motion (e.g. of the main sheath, each sub-arm, image sensor(s), and/or each instrument), and operation of the image sensor(s) and operation of each instrument may also be individually controlled through the user interface. User input (e.g. using the user interface) may be used to send commands and data to actuators that control the deployment, articulation, motion, and operation of the main sheath, individual sub-arms, the one or more image sensors, and instruments.

In some embodiments, a robotically driven medical system may include endolumenal devices, endoscopic devices, and/or laparoscopic devices. In some embodiments, the robotic medical device may be a single-port device. In "single port" devices, a single entry point on a patient's body may be used to perform medical procedures. The single entry point may be naturally occurring (e.g. oral, anal, etc.) or created via an incision made on the patient's body. For example, the main sheath (e.g. housing retracted sub-arms, image sensors, and instruments) may be inserted through the single port and robotically driven to a location of interest in the patient's body. The image sensors may be activated when in a housed/retracted state and captured images may be displayed to the user (as the main sheath is being robotically driven to the location of interest) using the visual interface to facilitate navigation of the robotic medical device through the patient's body. Flexibility and articulability of the main sheath may facilitate navigation through the body (e.g. through the gastro-intestinal (GI) tract, respiratory tract, etc.).

Images captured by the image sensor may be displayed to the user (e.g. a medical professional) using a visual interface such as a display or headset. In some embodiments, the display may be a 3-Dimensional (3D) (or stereoscopic) display and the image sensor may provide stereoscopic images. The user interface may also include a haptic interface for an operator of the robotically driven medical device to deploy, control, operate, and move the main sheath, sub-arms, the image sensor(s), and the individual instruments. The haptic interface and/or display may also be used provide feedback to the user. The feedback (haptic and/or visual) may be indicative of device, camera, and/or instrument state as described further herein. Haptic technology may be used to provide the haptic feedback. As used herein, the term haptic feedback refers to any technique of creating a tactile experience, which may include applying forces (e.g. resistance or assistance), vibrations, or other motion to an interface and/or component being operated by a user. Tactile sensors may be used to measure forces exerted by the user on the interface. Electrical, electronic, electromagnetic, and electromechanical techniques may be used to adjust the haptic feedback (e.g. forces, vibration, or motion) based on input from the tactile sensors.

In some embodiments, the user interface may be coupled to the robotically driven medical device (including the main sheath, sub-arms, the image sensor(s), and instruments) through a device control system. The device control system may receive commands from the user interface and control the medical device using a combination of electrical, electronic, electromagnetic, and/or electro-mechanical components.

In some embodiments, for one or more instruments, one or more corresponding instrument positions relative to a current field of view (FOV) of least one image sensor coupled to the robotic medical device may be obtained; and, for a selected instrument of the one or more instruments, generation of a corresponding feedback to a user may be initiated, wherein the corresponding feedback is based on a position of the selected instrument relative to the current FOV.

In some embodiments, the current FOV for at least one image sensor coupled to the robotic medical system may be obtained based on a corresponding current pose associated with the at least one image sensor. The field of view (FOV) of an image sensor at a point in time refers to the extent of the environment around the image sensor that can be observed by the image sensor. The FOV may be expressed as a solid angle. The image sensor may be sensitive to light (electromagnetic radiation) in the solid angle. FOV, as used herein, may also refer to an angle of coverage, which describes the angular range that the image sensor can effectively image. The angle of coverage for an image sensor may be smaller than the image sensor's theoretical FOV. Image sensor parameters (e.g. focal length, image sensor dimensions, etc.) may be used to determine the angle of coverage.

Further, the corresponding positions of one or more instruments relative to the current FOV may be determined based on: images captured by the at least one image sensor. For example, the corresponding positions of an instrument relative to the current FOV may be determined based on images captured by the at least one image sensor, when the position of the instrument lies within the current FOV. In some embodiments, a control model may be used to determine the corresponding positions of instruments relative to the current FOV based on user motion input from the start of a procedure, and/or from a time of image sensor, instrument, or sub-arm deployment. In some embodiments, sensor input from one or more (optional) sensors coupled to the robotic medical device may be used to determine the corresponding positions of instruments relative to the current FOV (e.g. when one or more of the instruments are outside the FOV).

In some embodiments, feedback may then be provided to the user, wherein the feedback is based on the corresponding positions of instruments relative to the current FOV. The feedback may comprise haptic and/or visual feedback. For example, the haptic feedback may be provided as haptic resistance to movement of the instrument in response to a determination that the position of the instrument is: (a) within a boundary of the current FOV and (b) within a threshold of the boundary of the current FOV, when the instrument is moved toward the boundary of the FOV. In some instances, the haptic resistance to movement of the instrument toward the boundary of the FOV may be inversely proportional to the distance between the boundary and the position of the instrument when the position of the instrument is within the current FOV and within the threshold of the boundary of the FOV. Haptic resistance may increase the effort or force needed to operate user controls that effect movement of a selected instrument.

As another example, the haptic feedback may be provided as haptic resistance to movement of the instrument in response to a determination that the position of the instrument is: outside the boundary of the current FOV and the instrument is moved further away from the boundary of the current FOV. In some instances, the haptic resistance to movement of the instrument further away from the current FOV boundary may be proportional to the distance between the boundary and the position of the instrument when the position of the instrument is outside the current FOV boundary.

In some embodiments, visual feedback may be provided by displaying a directional indicator indicating a corresponding movement direction for an instrument to bring the instrument further into the current FOV in response to a determination that the corresponding position of the instrument is within the current FOV and within a threshold of a boundary of the current FOV. As another example, visual feedback may be provided by displaying a directional indicator indicating a corresponding movement direction for an instrument to bring the instrument further into the current FOV in response to a determination that the corresponding position of the instrument is outside the boundary of the current FOV. In some embodiments, the magnitude of the directional indicator may be proportional to a distance between the corresponding position of the instrument and a specified location within the current FOV (e.g. the center or estimated center of the current FOV).

In some instances, the robotic medical system may disable functionality associated with an instrument when that instrument is outside the current FOV. For example, some instruments may be deemed or configured as preferably operated with user supervision and functionality associated with these instruments may be disabled when outside the current FOV. In some embodiments, the robotic medical system may be configured to automatically bring an instrument into the current FOV upon user request and/or for the duration of a procedure. In some embodiments, the robotic medical system may be configured to automatically track an instrument so that the instrument stays in the FOV of the image sensor for the duration of a procedure. For example, the image sensor may track instrument motion so that the instrument stays within some threshold of the FOV boundary. Thus, in some embodiments, when appropriately configured, motion of an image sensor may exhibit some correlation to the motion of a corresponding tracked instrument.

Conventional laparoscopic systems, which can be manual or non-robotic, may demand operator dexterity to operate the camera and instruments, which can be challenging. Additionally, conventional systems are limited by physician ergonomics, which can limit the physician's range of motion. For example, in conventional single port systems, many distinct instruments may be inserted through a single port, limiting the available range of motion for the camera and/or instruments thereby increasing procedural difficulty.

Multi-port systems, which require multiple incisions (e.g. one incision for each instrument), may allow increased range of motion, but increase recovery time. Moreover, in multi-port systems, ensuring that the distinct instruments remain in the camera FOV or bringing instruments into the FOV can be difficult and significantly increase operator cognitive load. In addition, in some conventional systems, an instrument may be coupled to a main arm that may be rigid and/or not independently maneuverable. The rigidity and/or non-maneuverability of the main arm may limit or increase the difficulty of many types of procedures that may be performed with conventional systems. For example, the GI tract includes many curves and bends, so a rigid and stiff main arm may limit procedures to the small straight section of the colon, the rectum, significantly reducing the capability of the device, and/or increasing the risk of tissue rupture.

FIG. 1A shows an example diagram illustrating some features of a robotic medical system 100 in accordance with certain embodiments disclosed herein.

In some embodiments, robotic medical system 100 may comprise user interface 130 (which may take the form of a user console), which may be electrically, electro-mechanically, and/or communicatively coupled to robotic medical device 200. Embodiments of robotic medical device 200 are described further in relation to FIGS. 2A-2C below. As shown in FIG. 1A, robotic medical device 200 may comprise main sheath 235, image sensors 110, and instruments 120 (e.g. instruments 120-1 and 120-2).

In some embodiments, the communicative coupling between user interface 130 and robotic medical device 200 may occur over a communications interface, which may be wired (e.g. wired communications interface 107) or wireless (e.g. wireless communication interface 105). The term "communications interface," as used herein, may refer to a wired communications interface or a wireless communications interface. For example, commands input by user using user interface 130 may be wirelessly communicated (e.g. over wireless communication interface 105) to a robotic medical device control system (e.g. robotic medical device control system 160 shown in FIG. 1B) associated with robotic medical device 200. In some embodiments, the robotic medical device control system may control and drive robotic medical device 200 based on commands received over the communications interface. Wired communication may occur using wired networks (including over the Internet and/or private networks), fiber optic interfaces, other widely available interfaces such as Universal Serial Bus (USB), Ethernet, Thunderbolt, and/or other proprietary interfaces. In some embodiments, wireless communication interfaces may include Wireless Personal Area Networks (WPANs) (e.g. based on the IEEE 802.15x standards) which may facilitate wireless communication between devices over short distances (e.g. within a room). Wireless communication may also include communication over Wireless Local Area Networks (WLAN), which may be based on the IEEE 802.11 standards, and/or over Wireless Wide Area Networks (WWAN), which may be based on cellular communication standards such as a Fifth Generation (5G) network, or Long Term Evolution (LTE). 5G and LTE based communication are described in documents available from an organization known as the 3rd Generation Partnership Project (3GPP). In some embodiments, a combination of wired and wireless communications may be used.

Thus, in some embodiments, a user interface 130 may be remotely situated from robotic medical device 200, and robotic medical device 200 may be controlled and operated based on input received by robotic medical device control system from user 130 over the communications interface. The robotic medical device control system (not shown in FIG. 1A) may control actuators and/or other electronic, electrical, electromagnetic, and/or electro-mechanical components associated with robotic medical device 200 based on the received commands (e.g. from user interface 130 over communications interface). In some embodiments, robotic medical system 100 may also include electrical coupling between user interface 130 (e.g. a user console) and robotic medical device 200 so that user interface 130 (e.g. the user console) may be electrically and communicatively coupled to robotic medical device 200 using some combination of wired and/or wireless links.

User interface 130 may comprise example haptic interface 140-1 and 140-2 (collectively referred to as haptic interface 140) and visual interface 135. In some embodiments, visual interface 135 may be stereoscopic and may comprise a 3D display and provide a 3D view of the environment around robotic medical device 200 (e.g. in embodiments where robotic medical device 200 includes stereoscopic image sensors 110). In some embodiments, In some embodiments, visual interface 135 may alternatively or additionally include a head mounted display. Visual interface 135 may also display an indication of the location of the robotic medical device 200 within the patient's body at various levels of granularity. Robotic medical device controls 145-1, 145-2, 145-3, and/or 145-4, (shown as foot pedals in FIG. 1A) may be used by the user to activate, deploy, select, control, and/or move one or more of main sheath 235, the sub-arms, image sensors 110, and/or instruments 120. For example, a user may use robotic medical device controls 145 (e.g. foot pedals) to select and activate an instrument 120, prior to moving the instrument 120 via haptic interface 140. Once the instrument 120 has been moved to a desired location, robotic medical device controls 145 (and/or haptic interface 140) may also be used to control instrument motion, instrument function, and perform procedures. In some embodiments, the selected component and/or the current function being performed using robotic medical device controls 145 may be displayed or indicated to the user (e.g. as an overlay) in visual interface 135.

Haptic interfaces 140 may each have degrees of freedom that reflect the degrees of freedom available to mother sheath 235, and/or the individual sub-arms, and/or image sensors 110, and/or instruments 120 on robotic medical device 200. In some embodiments, upon selection of one of the above components of robot medical device 200, haptic interface 140 may reflect the degrees of freedom available to the selected component. As shown in FIG. 1A, haptic interfaces 140-1 and 140-2 may be moved and/or oriented in various directions, as indicated in FIG. 1A by directional arrows reflecting motion related user input 143-1 and 143-2, respectively. Haptic interfaces 140 may also include other mechanisms to provide user input (e.g. triggers, buttons, thumb wheels, etc.) to control the mother sheath 235, the various sub-arms individually, the instruments 120 and/or the image sensors 110. In some embodiments, one haptic interface (e.g. 140-2) may be used to articulate/move a selected component (e.g. mother sheath 235, sub-arms, selected instrument 120, and/or image sensors 110), while the other (e.g. 140-1) may be used to exercise control over the function of the instrument 120 and/or to provide other input.

The movements of haptic interfaces 140 (e.g. by a user) may be mirrored by one or more of mother sheath 235, sub-arms, image sensors 110, and/or instruments 120 on robotic medical device 200 (depending on the currently active and/or selected component(s)). In some embodiments, users may configure robotic medical system 100 to a desired sensitivity so that movements of selected and/or active instruments appropriately reflect user movement of haptic interfaces 140. The term "degrees of freedom" refers to the number of independent parameters that determine the pose of an object. The term "pose" refers to the position (e.g. X, Y, Z coordinates) and orientation (e.g. roll, pitch, and yaw) of an object relative to a frame of reference. Pose may be specified as a 6 Degrees-of-Freedom (DOF) pose, which may include positional coordinates (e.g. X, Y, Z) and orientation information (e.g. roll, pitch, and yaw) relative to a frame of reference. In some embodiments, haptic interface 140 may be used to articulate, move, and orient one or more of main sheath 235, the individual sub-arms, image sensors 110, and/or instruments 120-1 and 120-2. For example, haptic interface 140 may be used to place image sensors 110 in a specified pose. The term "camera pose" or "image sensor pose" may refer to the position and orientation of the image sensor relative to a frame of reference. The image sensor pose may be used to determine a field of view of the image sensor. The field of view of the image sensor may be expressed in mathematical form (e.g. as a conical section). In some embodiments, the frame of reference may be image sensor centric and may be used to express: (a) the field of view of the image sensor, relative to the (image sensor centric) frame of reference and/or (b) the position and orientation of one or more instruments 120. Instrument positions may thus be determined relative to the field of view (e.g. whether inside the FOV, outside the FOV, location relative to a boundary of the FOV, etc.).

In some embodiments, haptic interfaces 140 may also provide haptic feedback 141 (FIG. 1B) to the user. Tactile sensors may be used to measure forces exerted by the user on the interface. Electrical, electronic, electromagnetic, and electromechanical techniques may be used to adjust the haptic feedback (e.g. forces, vibration, or motion) based on input from the tactile sensors. In some embodiments, the haptic feedback 141 provided to the user may be based on the corresponding positions of instruments 120 relative to the current FOV of image sensors 110. For example, the haptic feedback 141 may be provided as haptic resistance to movement of the instrument 120 in response to a determination that the position of the instrument 120 is: (a) within a boundary of the current FOV and (b) within a threshold of the boundary of the current FOV, when the instrument is moved toward the boundary of the current FOV. In some instances, the haptic resistance to movement of the instrument 120 toward the boundary may be inversely proportional to the distance between the boundary and the position of the instrument 120 when the position of the instrument 120 is within the current FOV and within the threshold of the boundary of the current FOV. In some embodiments, as outlined above, haptic interface 140 may include buttons, triggers, or other mechanisms to accept user input. For example, the user may configure robotic medical device 200 (e.g. by setting parameters in configuration information 177) so that one or more instruments 120 may be automatically positioned (e.g. centered) within the current FOV upon user input—such as by activating a trigger or pressing a button on haptic interface 140.

As another example, the haptic feedback 141 may be provided as haptic resistance to movement of the instrument 120 in response to a determination that the position of the instrument 120 is: outside the boundary of the current FOV and the instrument 120 is moved further away from the boundary of the current FOV. In some instances, the haptic resistance to movement of the instrument 120 further away from the current FOV boundary may be proportional to the distance between the boundary and the position of the instrument 120 when the position of the instrument 120 is outside the current FOV boundary.

Thus, the haptic feedback 141 may provide the user with a real-time interactive indication of the current FOV boundary, when the user attempts to move one or more instruments 120 in direction that would result in the instruments 120 being out of the current FOV of the image sensors 110 or closer to the edge of the FOV (when the instruments 120 are currently in view), or when one or more instruments 120 not currently in the FOV are moved in a direction further away from the current FOV.

Figure 1B:
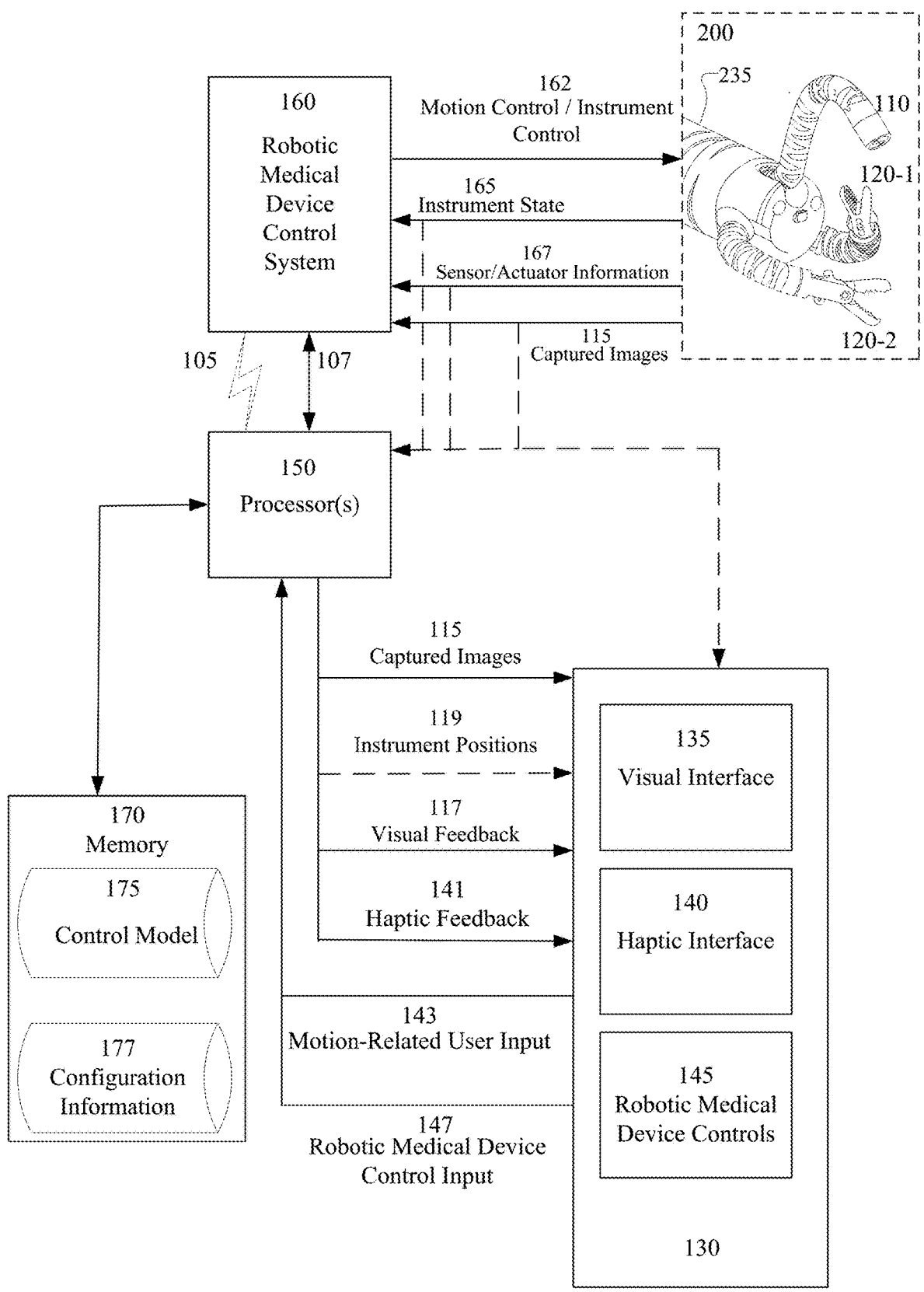
FIG. 1B shows a schematic block diagram illustrating functional blocks of a robotic medical system in accordance with certain embodiments disclosed herein.

In some embodiments, visual interface 135 may also be used to provide visual feedback 117 (FIG. 1B). For example, visual feedback 117 may be provided by displaying a directional indicator indicating a corresponding movement direction to bring one or more instruments 120 further into the current FOV in response to a determination that the corresponding position of the instrument 120 is within the current FOV and within a threshold of a boundary of the current FOV. As another example, visual feedback 117 may be provided by displaying a directional indicator (e.g. an arrow) indicating a corresponding movement direction for an instrument 120 to bring the instrument 120 into the current FOV in response to a determination that the corresponding position of the instrument 120 is outside the boundary of the current FOV. In some embodiments, the magnitude of the directional indicator may be proportional to a distance between the corresponding position of the instrument 120 and a specified location within the current FOV (e.g. the center or estimated center of the current FOV).

FIG. 1B shows an example schematic block diagram illustrating some functional blocks of a robotic medical system in accordance with certain embodiments disclosed herein. As shown in FIG. 1B, robotic medical system 100 may comprise visual interface 135 (e.g. a display headset, a 3D display or stereoscopic display, etc.), haptic interface 140, and robotic medical device controls 145. Visual interface 135, haptic interface 140, and robotic medical device controls 145 have been described above in relation to FIG. 1A).

Robotic medical system 100 may further include processor(s) 150, memory 170, robotic medical device control system 160, and robotic medical device 200 (as described further below in relation to FIGS. 2A-2C). FIG. 1B is merely exemplary and the functionality associated with blocks shown in FIG. 1B may be combined (e.g. into a single block), or the functionality in a block may be distributed across several blocks. For example, the functionality associated with robotic medical device control system block 160 may be integrated within processor(s) 150 block or vice versa. As another example, the functionality associated with processor(s) 150 block and user interface block 130 may be combined. As a another example, the functionality associated with processor(s) 150 block, user interface block 130, and robotic medical device control system block 160 may be combined. As a further example, the functionality associated with processor(s) 150 block may be distributed between robotic medical device control system block 160 and user interface block 130.

Haptic Interface 140 may provide motion-related user input 143 to processor(s) 150 based on user motion. As outlined above, user motion may be received by processor(s) 150 as motion-related user input 143 and communicated to robotic medical device control system 160, which may process the received input and provide appropriate signals to articulate/move the selected and/or active component (one or more of main sheath 235, sub-arms, image sensors 110, and/or instruments 120). Haptic feedback 141 (e.g. based on the position of instruments 120 relative to the current FOV of image sensors 110) may be provided to the user via haptic interface 140.

User operation of robotic medical device controls 145 (e.g. as described above in relation to FIG. 1A) may provide robotic medical device control input 147 to processor(s) 150, which may be processed and communicated to robotic medical device control system 160. Robotic medical device control system 160 may further process the received robotic medical device control input 147 and provide as motion control/instrument control input 162 to robotic medical device 200. Motion control/instrument control input 162 may include appropriate signals to select, activate, deploy, retract, disable, and/or enable a robotic medical device component (e.g. one or more of main sheath 235, image sensors 110, and/or instruments 120).

In some embodiments, processor(s) 150 may be coupled to memory 170. As shown in FIG. 1B, memory 170 may include control model 175, which may be used by processor (s) 150 to determine the positions of instruments 120 relative to image sensors 110. In some embodiments, control model 175 may include calibrated instrument control models, which may be used to estimate instrument position relative to an image sensor pose and/or a current FOV of image sensors 110. In some embodiments, control model 175 may be configured to make use of information in captured images 115 (e.g. when one or more instruments are visible in the FOV of image sensor 110) when being used (e.g. by processor(s) 150) to determine instrument positions relative to the FOV of image sensors 110.

In some embodiments, images captured by image sensors 110 may be processed using object recognition and/or tracking techniques (e.g. by processor(s) 150) to determine a location of one or more instruments 120 in the current FOV of image sensor 110. In some embodiments, based on configuration information 177 (e.g. as set or invoked by a user), object tracking techniques may also be used to keep an instrument 120 in the FOV of image sensors 110 during a procedure (or portion of a procedure). Object tracking techniques may use one or more of: control model 175, the known instrument form factor and/or other instrument characteristics, in conjunction with image processing and computer vision techniques to locate an instrument 120 in captured images 115. Image sensors 110 may be moved to keep the instrument 120 in the FOV of image sensors 110. Because the form factors of instruments 120 coupled to robotic medical device 200 are known, object recognition and tracking techniques may be applied to identify instruments 120 in a sequence of image(s) captured by image sensors 110 and determine their respective locations relative to the image sensors and/or the corresponding image sensor FOV. In some embodiments, instruments 120 and/or sub-arms may include known markers (e.g. registration markers) to facilitate instrument identification, tracking, and location determination (e.g. relative to the camera centric frame of reference).

In some embodiments, sensor/actuator information 167, instrument state 165, and captured images 115 may be provided (e.g. by robotic medical device control system 160) to processor(s) 150 and/or user interface 130.

In some embodiments, instrument positions 119 may be determined (e.g. by processor(s) 150 using control model 175) based on one or more of: sensor/actuator information 167, configuration information 177, prior motion-related user input 143, and/or instrument state 165. In some embodiments, instrument positions 119 (e.g. as determined by processor(s) 150 and/or robotic medical device control system 160) may be made provided to user interface 130. In some embodiments, processor(s) 150 and/or user interface 130 may determine instrument positions 119 independently based on one or more of: sensor/actuator information 167, configuration information 177, prior motion-related user input 143, and/or instrument state 165 (e.g. by invoking control model 175).

Configuration information 177 may provide information pertaining to the instruments 120 on robotic medical device 200, image sensor configuration (e.g. lens focal length and other parameters), user preferences (e.g. sensitivity to user movement, the desired level of haptic feedback 141, automatic maintenance of FOV over instruments 120, display parameters, etc.) and/or an operational configuration or mode of operation of robotic medical system 100. Configuration information 177 may further indicate whether functionality (or a portion of the functionality) of one or more instruments 120 is to be disabled when not in the current FOV of image sensor(s) 110.

In some embodiments, control model 175 may also use sensor/actuator information 167 from one or more sensors and actuators (when present) in robotic medical device 200. Sensor/actuator information 167 may provide information pertaining to the state of sensors/actuators coupled to robotic medical device 200. Sensor/actuator information 167 may be used by control model 175 to determine the corresponding current poses (positions and orientations) of instruments 120. The sensors coupled to robotic medical device 200 may include one or more of: electronic sensors; electromagnetic sensors; electro-mechanical sensors, including micro-electro mechanical sensors (MEMS). The sensors may be used to sense actuator articulation/motion of the main sheath, and/or of image sensors 110 and/or the image sensor sub-arm, and/or instruments 120 and/or the instrument sub-arms. The sensors may include 3D shape sensing fiber optic sensors; fiber optic force and/or pressure sensors such as photonic crystal fiber (PCF) sensors or Fiber Bragg Grating (FBG) sensors, or make use of scattering arising from FBG sensors, inherently present, or make use of post-process produced Rayleigh scattering. In some embodiments, sensor/actuator information 167 from one or more sensors may be used in conjunction with captured images 115 and/or user motion input to determine instrument pose or instrument positions. In some embodiments, the instrument pose and/or instrument positions determined above may be relative to the image sensor centric frame of reference.

In some embodiments, the sensors coupled to robotic medical device 200 may form part of a tracking and pose determination system. Electromagnetic sensors may be embedded in instruments 120 and/or at one or more locations in the image sensor sub-arm and instrument sub-arms. Electromagnetic sensors may use an electromagnetic field generator and small electromagnetic coils to track the instruments. Input from the electromagnetic sensors may be processed (e.g. using signal processing techniques) to determine and track the poses of one or more instruments 120. In some embodiments, signal processing techniques may compensate for distortions in sensor readings that may be caused by the presence of non-magnetic conductive materials in the environment. Electromagnetic tracking and pose determination techniques may operate to determine pose even in situations where there is no line of sight to instruments 120 and/or when one or more instruments are outside the FOV of image sensors 110. In some embodiments, input from the electromagnetic sensors may be used by control model 175 to determine a pose (or relative pose) of one or more instruments 120.

In some embodiments, captured images 115 (e.g. by image sensors 110) may be processed using object recognition and/or tracking techniques (e.g. by processor(s) 150) to determine a location of one or more instruments 120 in the current FOV of image sensors 110. Because the form factors of instruments 120 coupled to robotic medical device 200 and their corresponding deployment state are known, the above information may be used processor(s) 150 executing control model 175 to determine locations of instruments 120 coupled to robotic medical device 200 in captured images 115, and/or to track the positions of the instruments over a sequence of images without the need for external markers. As another example, instruments 120 and/or instrument sub-arms may include registration marks, which may be detected in captured images 115 and used to track instruments and/or determine pose. Thus, tracking and pose determination techniques may be markerless (e.g. based on the known form factors of instruments) or involve the use of registration marks. In some embodiments, control model 175 may be used to determine instrument pose based on some combination of captured images 115, and/or sensor/actuator information 167 (which may include input from one or more of electromagnetic sensors, electro-mechanical sensors, electronic sensors, 3D shape sensing fiber optic sensors; fiber optic force and/or pressure sensors etc.).

In some embodiments, image processing techniques such as object recognition and tracking techniques may be applied to identify instruments 120 in image(s) captured by image sensors 110 and to determine their respective locations relative to the image sensors and/or the corresponding image sensor FOV. Object recognition and tracking techniques may include feature extraction from images, feature matching/tracking, image comparison, image matching, image differencing, pattern recognition, etc. As outlined above, in situations where: (a) there is no line of sight to instruments 120 (e.g. line of sight is obscured by tissue or other obstructions), there is no line of sight to instruments 120; and/or (b) one or more instruments are outside the FOV of image sensors 110, then electromagnetic tracking and pose determination techniques may operate to track instruments 120 and determine pose In some embodiments, processor(s) 150 may use control model 175 and one or more of: motion-related user input 143, robotic medical device control input 147, captured images 115, configuration information 177, and/or sensor/actuator information 167 to determine a pose of image sensor 110 and a current FOV of image sensor 110 relative to a frame of reference, and/or the position of instruments 120 relative to the current FOV of image sensor 110.

Although shown as separate from processor(s) 150, memory 170 may be external and/or internal to processor(s) 150 and may include primary and/or secondary memory. Program code may be stored in memory 170, and read and executed by processor(s) 150 to perform the techniques disclosed herein. As used herein, the term "memory" refers to any type of long term, short term, volatile, nonvolatile, or other memory and is not to be limited to any particular type of memory or number of memories, or type of media upon which memory is stored. Examples of storage media include computer-readable media encoded with databases, data structures, etc. and computer-readable media encoded with computer programs. Computer-readable media may include physical computer storage media. A storage medium may be any available medium that can be accessed by a computer. By way of example, and not limitation, such computer-readable media can comprise Random Access Memory (RAM) and variations thereof including Non-Volatile RAM (NVRAM), Read Only Memory (ROM) and variations thereof Erasable Programmable (EPROM), Flash Memory, etc. Computer-readable media may also include Compact Disc ROM (CD-ROM), memory cards, portable drives, or other optical disk storage, magnetic disk storage, solid state drives, other storage devices, or any other medium that can be used to store desired program code in the form of instructions and/or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

In some embodiments, processor(s) 150 may process robotic medical device control input 147 and motion-related user input 143. The processed information may be sent to robotic medical device control system 160 (e.g. via wireless communications interface 105 and/or wired communications interface 107). Robotic medical device control system 160 may process the information received from processor(s) 150 and send signals to appropriate actuators on robotic medical device 200 to control, articulate/move, retract, deploy, and/or invoke functionality associated with one or more of: main sheath 235, sub-arms, image sensors 110, and/or instruments 120.

Although shown in FIG. 1B as discrete blocks, processor(s) 150 and/or memory 170 may be distributed between robotic medical device control system 160 and user console 130 (e.g. comprising Visual Interface 135, haptic interface 140, and robotic medical device control 145). In one embodiment, robotic medical device control system 160 and user console 130 may each have individual local processors 150. For example, when user console 130 is remotely situated from robotic medical device 200, user console 130 and robotic medical device 200 may each have local processors 150. Accordingly, in one embodiment, local processors associated with user console 130 may be configured to: (a) obtain and transmit motion-related user input 143 and robotic medical device control input 147 to local processors associated with robotic medical device control system 160; and (b) receive and display captured images 115 and provide visual feedback 117 using visual interface 135, and provide haptic feedback 141 based on input received from robotic medical device control system 160 (e.g. one or more of: instrument state 165, sensor/actuator information 167, captured images 115, and/or image sensor pose, FOV, and instrument position). Conversely, local processors associated with robotic medical device control system 160 may be configured to: (a) receive motion-related user input 143 and robotic medical device control input 147 from local processors associated with user console 130 and provide appropriate motion control/instrument control input 162 to robotic medical device 200 (e.g. based on the received motion-related user input 143 and robotic medical device control input 147); and (b) obtain and transmit captured images 115, instrument state 165, and sensor/actuator information 167 (and/or determined image sensor pose, current FOV, and instrument position information) to local processors associated with user console 130. As another example, memory 170 and functionality associated with processor(s) 150 may be shared between user console 130 and robotic medical device control system 160.

In some embodiments, robotic medical device control system 160 may also obtain sensor/actuator information 167 from sensors/actuators on robotic medical device 200, captured images 115 from image sensors 110, and instrument state 165. Sensor/actuator information 167, captured images 115, and instrument state 165 may also be received by processor(s) 150 either directly (when coupled to robotic medical device 200) or indirectly from robotic medical device control system 160 (e.g. over wireless communication interface 105/wired communications interface 107). Robotic medical device control system 160 may control actuators and/or other electronic, electrical, and electromechanical components associated with robotic medical device 200 based on the received commands (e.g. motion-related user input 143 and robotic medical device control input 147). In some embodiments, robotic medical device control system 160 may include functionality to detect and prevent collisions, entanglements, and/or physical contract between sub-arms. For example, sections of the main sheath and/or one or more sub-arms may be reconfigured (e.g. without change to the final poses of the image sensors 110 and/or instruments 120) to avoid collisions, contact, or entanglement.

The methodologies described herein may be implemented in hardware, firmware, software, or any combination thereof. For a hardware implementation, the processor(s) 150 may be implemented within one or more application specific integrated circuits (ASICs), digital signal processors (DSPs), image processors, digital signal processing devices (DSPDs), programmable logic devices (PLDs), field programmable gate arrays (FPGAs), processors, controllers, micro-controllers, microprocessors, electronic devices, other electronic units designed to perform the functions described herein, or any combination thereof. In some embodiments, processor(s) 150 may include capabilities to: determine a FOV for image sensors 110, determine a pose of image sensor 110, determine a FOV associated with image sensors 110, process images, determine and track corresponding positions of instruments relative to a current image sensor FOV, provide input to control haptic feedback 141, provide visual feedback 117, and provide input to control actuators on robotic medical device 200. Processor(s) 150 may also include functionality perform other well-known computer vision and image processing functions such as feature extraction from images, image comparison, image matching, object recognition and tracking, image compression and decompression, etc.

Figure 2A:
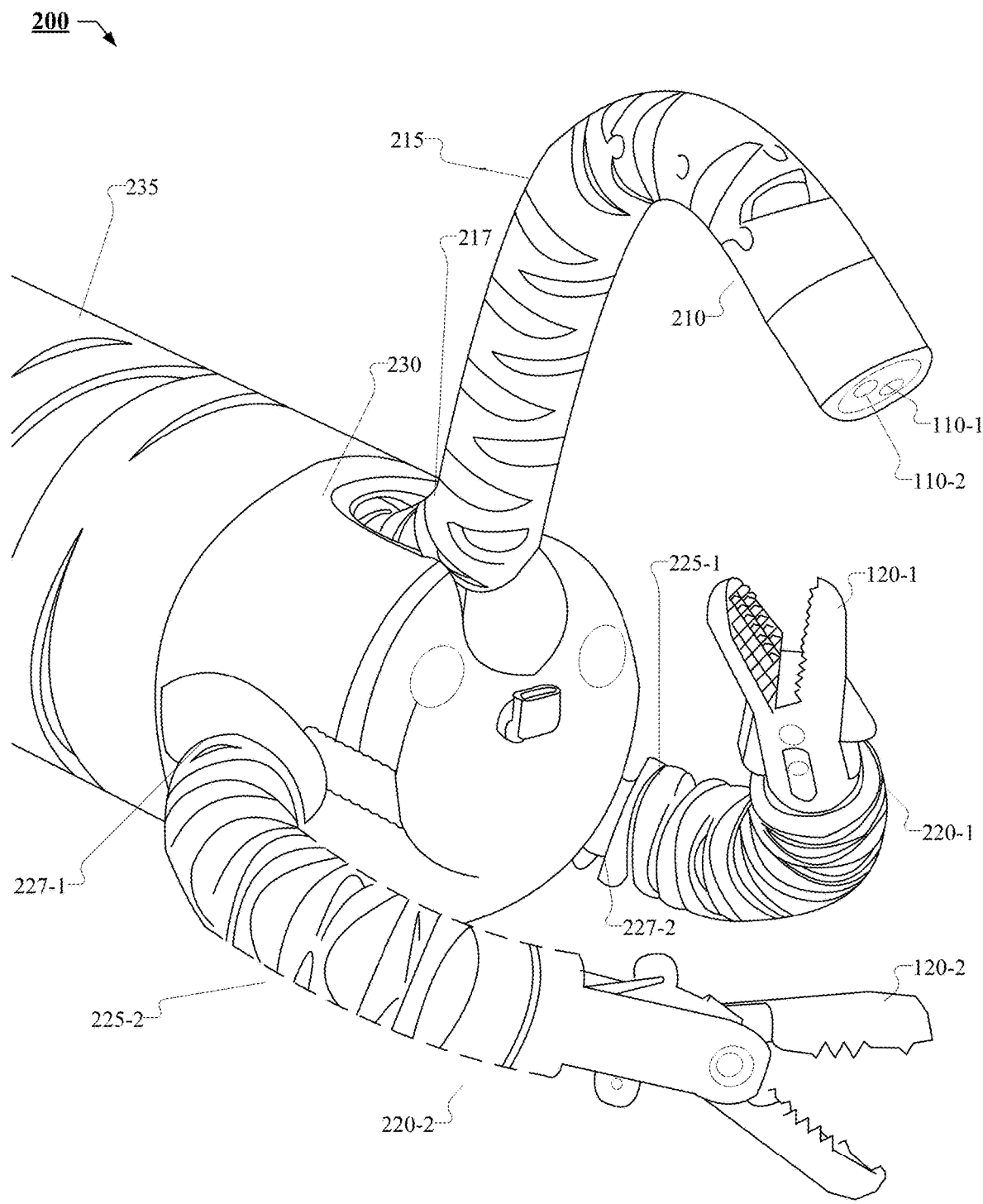
FIG. 2A shows an example robotic medical device with a flexible articulating main sheath coupled to image sensors and a plurality of instruments in accordance with certain embodiments disclosed herein.
Figure 2B:
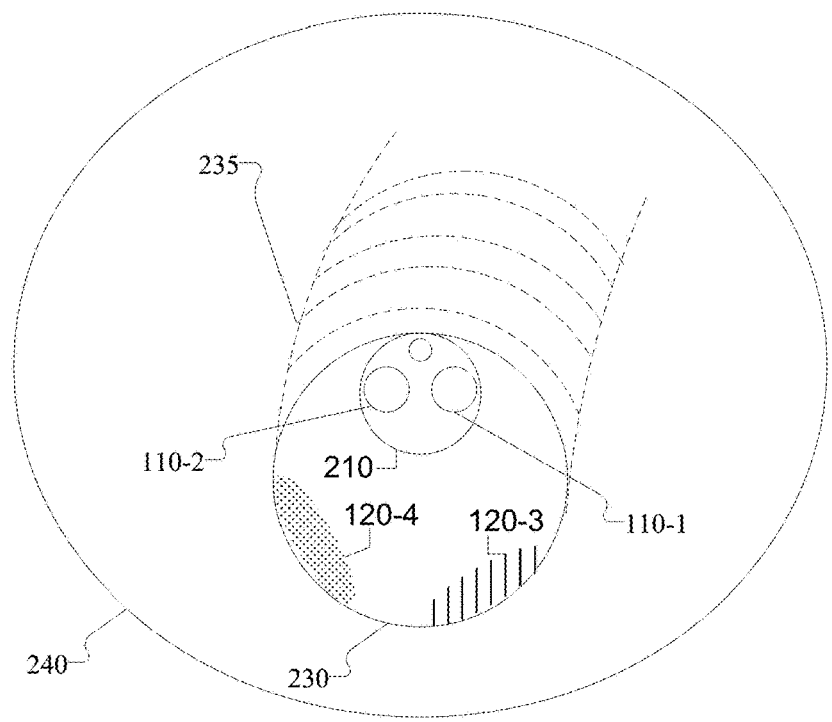
FIG. 2B shows a diagram illustrating image sensors and instruments of an example robotic medical device in a retracted state.

FIG. 2A shows image sensors 110 and instruments 120 coupled to the distal end 230 of a flexible articulating main sheath 235 of a robotic medical device 200 in accordance with certain embodiments disclosed herein. In some embodiments, robotic medical device 200 may form part of an endolumenal device, an endoscopic device, or a laparoscopic device. Robotic medical device 200 may form part of a robotically driven medical system or another robotic device and may facilitate visualization of instruments 120 during medical procedures In some embodiments, a robotic device may include robotic medical device 200, user-interface 130 (not shown in FIG. 2A) to facilitate user interaction with robotic medical device 200, and processor(s) 150 (not shown in FIG. 2A) coupled to robotic medical device 200 and the user interface 130.

Further, as shown in FIG. 2A, robotic medical device 200 may include: (a) flexible articulating main sheath 235; (b) flexible independently articulable image sensor sub-arm 215, wherein a proximal end 217 of the image sensor sub-arm 215 is coupled to a distal end 230 of the main sheath 235; (c) a plurality of flexible independently articulable instrument sub-arms 225 (e.g. 225-1 and 225-2), wherein each instrument sub-arm (e.g. 225-1 or 225-2) has a corresponding proximal end 227 (e.g. 227-1 or 227-2, respectively) coupled to the distal end 230 of the main sheath 235; (d) at least one image sensor 110 (with image sensors 110-1 and 110-2), wherein the at least one image sensor 110 is coupled to a distal end 210 of the image sensor sub-arm 215; and (e) a plurality of instruments 120 (e.g. 120-1 and 120-2), wherein each instrument (120-1 or 120-2) is coupled to a distal end 220 (e.g. 220-1 or 220-2, respectively) of a corresponding instrument sub-arm (e.g. 225-1 or 225-2, respectively) of the plurality of instrument sub-arms 225 (e.g. 225-1 and 225-2).

The processor(s) 150 on the robotic device may be configured to determine, based on a corresponding current pose associated with the at least one image sensor 110, a current FOV of the at least one image sensor 110; determine, for an instrument (120-1 or 120-2) in the plurality of instruments (e.g. 120-1 and 120-2), a position of the instrument (120-1 or 120-2) relative to the current FOV based, at least in part, on captured images 115 captured by the at least one image sensor 110; and provide feedback using the user-interface 130, wherein the feedback is based on the corresponding position of the instrument (120-1 or 120-2, respectively) relative to the current FOV. The user interface 130 may include at least one of: a haptic interface 140, and/or a visual interface 135 and the feedback may include haptic feedback 141 using provided using the haptic interface, 140 or visual feedback 117 using the visual interface 135; or a combination of visual feedback 117 and haptic feedback 141. A proximal end of main sheath 235 (not shown in FIG. 2A) may be coupled (electrically, electronically, electromagnetically, and/or electro-mechanically) to robotic medical device control system 160 and/or processor(s) 150. Embodiments of robotic medical device 200 are described further below.

For example, as shown in FIG. 2A, robotic medical device 200 may comprise a user-controlled robotically driven flexible articulating main sheath 235 (also referred to as "mother sheath"). Main sheath 235 may be selected and controlled by the user using processor(s) 150. In some instances, processor(s) 150 may form part of user interface 130 and/or robotic medical device control system 160. In some embodiments, main sheath 235 may be selected and controlled by the user using user interface 130, which may include robotic medical device controls 145 (FIG. 1A) and/or and haptic interface 140 (e.g. haptic interfaces 140-1 and/or 140-2).

Main sheath 235 may be flexible, independently articulable at various locations on main sheath 235, and capable of movement in various directions based on user input provided, for example, by motion-related user input 143 using haptic interface 140. Main sheath 235 and sub-arms (215 and/or 225) may be articulated independently. Further, the movement of a sub-arm (215 and/or 225) may occur independently (e.g. without movement) of main sheath 235 and without movement of another sub-arm. Main sheath 235, image sensor sub-arm 215, and instrument sub-arms 225 may each include actuators at various locations to facilitate independent articulation and/or movement of the main sheath and/or corresponding sub-arm. Further, in some embodiments, actuators may facilitate pivoting (e.g. pitch)

of image sensor 110 without articulation/motion of image sensor sub-arm 215 and instruments 120 may be capable of pivoting (pitch) and/or rotation (roll) without articulation/motion of the corresponding instrument sub-arms 225. Actuators may (directly or indirectly) receive individual commands from processor(s) 150 based on user-input (e.g. provided using user-interface 130).

Main sheath may be recessed and capable of housing sub-arms and image sensors 110/instruments 120 coupled to the sub-arms when the sub-arms are in a retracted state. Main sheath may also house wires, cables, actuators, sensors etc. For example, image sensor sub-arm 215 and each instrument sub-arm 225 may be retracted and housed when retracted (e.g. in recesses) in main sheath. In some embodiments, input provided to actuators may be used along with control model 175 to determine corresponding positions of instruments 120 relative to a current pose of image sensors 110. In some embodiments, input from electro-mechanical sensors coupled to the actuators and/or sub-arms may be obtained by processor(s) 150 and used, in part, to determine corresponding positions of instruments relative to a current pose of image sensors 110.

Thus, main sheath 235 may be articulated (bent in a user-controlled manner at one or more specific locations on the main sheath 235), moved in various directions, and/or rotated by the user using haptic interface 140 and/or robotic medical device controls 145. For example, articulating the main sheath 235 at one or more locations may facilitate navigation/positioning of image sensors 110 and instruments 120 in a patient's gastro-intestinal (GI) tract close to an area of attention in the GI tract.

In some embodiments, as shown in FIG. 2A, a distal end 230 of main sheath 235 may be coupled to a proximal end 217 of flexible articulating image sensor sub-arm 215, and to corresponding proximal ends 227-1 and 227-2 of flexible articulating instrument sub-arms 225-1 and 225-2, respectively. As shown in FIG. 2A, image sensor sub-arm 215 may be flexible and independently capable of articulating in various directions. A distal end 210 of the image sensor sub-arm 215 may be coupled to one or more image sensors 110. For example, as shown in FIG. 2A, image sensors 110-1 and 110-2 are coupled to the distal end 210 of image sensor sub-arm 215. Image sensor sub-arm 215 may be selected and controlled by the user using robotic medical device controls 145 (FIG. 1A) and haptic interface 140 (e.g. haptic interfaces 140-1 and/or 140-2 in FIG. 1A). For example, image sensor sub-arm 215 may be independently (e.g. independently of any other sub-arm 225 and/or independently of main sheath 235) articulated (bent in a user-controlled manner at one or more specific locations on the image sensor sub-arm 215), retracted and housed when retracted within main sheath 235, or operationally deployed. FIG. 2A shows image sensor sub-arm 215 in a deployed state.

In some embodiments, as shown in FIG. 2A, distal end 230 of main sheath may be coupled to a proximal end 227-1 of flexible articulating instrument sub-arm 225-1 and to a proximal end 227-2 of flexible articulating instrument sub-arm 225-2. As shown in FIG. 2A, instrument sub-arms 225-1 and 225-2 may be flexible and capable of articulating independently in various directions. A distal end 220-1 of instrument sub-arm 225-1 may be coupled to instrument 120-1 (shown as a grasper in FIG. 2A). A distal end 220-2 of instrument sub-arm 225-2 may be coupled to another instrument 120-2 (shown as a grasper in FIG. 2A). Instrument sub-arms 225-1 and 225-2 may be selected and controlled by the user using robotic medical device controls 145 (FIG. 1A) and haptic interface 140 (e.g. haptic interfaces 140-1 and/or 140-2). For example, instrument sub-arms 225-1 (or 225-2) may be articulated (bent in a user-controlled manner at one or more specific locations on the image sensor sub-arm 225-1 (or 225-2) and independently of the image sensor sub-arm 215, and any other sub-arm, and/or main sheath 235), retracted, or deployed. Instrument sub-arms 225-1 and 225-2 may each be moved (independently of main sheath 235) in various directions and/or rotated by the user using haptic interface 140 and/or robotic medical device controls 145. Instrument sub-arms 225-1 and 225-2 may be retracted and housed when retracted within main sheath 235. FIG. 2A shows instrument sub-arms 225-1 and 225-2 in a deployed state.

In some embodiments, robotic medical system 100, and/or processor(s) 150, and/or robotic medical device control system 160 (FIG. 1B) may include functionality to detect and prevent collisions, entanglements, and/or physical contact between any of: image sensors 110, image sensor sub-arm 215, instrument 120-1, instrument sub-arm 225-1, instrument 120-2, and/or instrument sub-arm 225-2. For example, sections of the main sheath and/or one or more sub-arms may be reconfigured (e.g. without change to the final poses of the image sensors 110 and/or instruments 120) to avoid collisions, contact, or entanglement In some embodiments, robotic medical device 200 may optionally include electro-magnetic sensors, 3D shape sensing fiber optic sensors, fiber optic force and/or pressure sensors such as photonic crystal fiber (PCF) sensors or Fiber Bragg Grating (FBG) sensors, or make use of scattering arising from FBG sensors or inherently present, or make use of post-process produced Rayleigh scattering (not shown in FIG. 2A). Input from one or more of the above sensors may be used to determine a pose (or relative pose) of instruments 120 and/or instrument sub-arms 225.

Main sheath 235 and/or image sensor 215 may also include light sources to illuminate an environment around robotic medical device 200. Image sensors 110 may include cameras, CCD sensors, or CMOS sensors, which may transform an optical image into an electronic or digital image and may send captured images 115 to processor 150. In some embodiments, image sensors 110 may capture color images, which provide "color information," while "depth information" may be provided by a depth sensor. The term "color information" as used herein refers to color and/or grayscale information. In general, as used herein, a color image or color information may be viewed as comprising 1 to N channels, where N is some integer dependent on the color space being used to store the image. For example, an RGB image may be viewed as comprising three channels, with one channel each for Red, Blue, and Green information. In some embodiments, depth information may be captured using depth sensors (active or passive). The term "depth sensor" is used to refer to functional units that may be used to obtain depth information independently and/or in conjunction with image sensors 110.

In some embodiments, image sensors 110-1 and 110-2 may form a (passive) stereoscopic image sensor, and may capture stereoscopic images, which may be used to determine depth information. Accordingly, in some embodiments, captured images 115 (FIG. 1B) may include stereoscopic or 3D images with depth information. For example, pixel coordinates of points common to both image sensors (e.g. 110-1 and 110-2) in a captured image may be used along with triangulation techniques to obtain per-pixel depth information. In some embodiments, the depth information may be used, in part, to determine the pose of instruments 120 relative to image sensors 110.

Accordingly, in some embodiments, robotic medical device 200 may include at least one image sensor 110 (e.g. a stereoscopic sensor or 3D image sensor), a plurality of instruments 120 (e.g. grasper 120-2, cautery knife, etc.), and one or more sensors (e.g. some combination of electromagnetic sensors; or electro-mechanical sensors; or 3D shape sensing fiber optic sensors; or fiber optic force sensors; or fiber optic pressure sensors; or a combination thereof). Further, in some embodiments, the electro-mechanical sensors may include micro electro-mechanical sensors (MEMS); and the fiber optic force sensors and the fiber optic pressure sensors may include one or more of: photonic crystal fiber (PCF) sensors or Fiber Bragg Grating (FBG) sensors. The image sensors 110 may be coupled to a distal end 210 of flexible articulating image sensor sub-arm 215, and instruments 120 may be coupled to corresponding distal ends 220 of flexible articulating instrument sub-arms 225. The proximal end 217 of flexible articulating image sensor sub-arm 215 and proximal end of flexible articulating instrument sub-arms may be coupled to a distal end 230 of flexible articulating main sheath 235. The image sensor sub-arm 215 and the plurality of instrument sub-arms 225 may be retractable into the main sheath and housed in the main sheath (e.g. during deployment, prior to activation, or upon deactivation). Image sensors 110 may be activated even when the image sensor sub-arm 215 is in a retracted state so that an operator of robotic medical device may be able to capture and view images of an environment around robotic medical device 200 even when the image sensor sub-arm is in a retracted state.

Robotic medical device 200 may further include a plurality of actuators (not shown in FIG. 2A) coupled to a flexible articulating main sheath 235, image sensors 110, instruments 120, flexible articulating image sensor sub-arms 215, flexible articulating instrument sub-arms 225 to control, extend, retract, articulate, and effect movement of the above components. The sensors and actuators may be disposed at various locations on robotic medical device 200 including at various locations on image sensor sub-arm 215 and instrument sub-arms 225 based on design parameters such as the desired accuracy and precision of position detection, level of articulation and/or movement desired. Each actuator may be responsive to commands from a processor(s) 150 or robotic medical device control system 160, which may be based on input from user interface 130. The plurality of actuators may facilitate independent articulation and independent motion of the main sheath, the image sensor sub-arm, and the plurality of instrument sub-arms based on the received commands. Actuators may also be used to provide haptic feedback FIG. 2B shows a diagram illustrating image sensors 110 and instruments 120, which are coupled to the distal end 230 of a flexible articulating main sheath 235 of a robotic medical device 200, in a retracted state and housed in main sheath 235. Image sensor sub-arm 215 (not visible in FIG. 2B) with image sensors 110 and instrument sub-arms 225-4 and 225-5 (not visible in FIG. 2B) with instruments 120-3 and 120-4, respectively, may be retracted into recesses in main sheath 235 and housed in main sheath 235 when retracted. For example, when robotic medical device 200 is being deployed and moved a location (e.g. within a patient's GI tract 240), image sensor sub-arm 215 and instrument sub-arms 225-3 and 225-4 may be retracted so that image sensors 110 and instruments 120 are housed within main sheath 235 thereby facilitating maneuverability of the flexible main sheath 235 (through the GI tract 240) and faster and easier movement and deployment of robotic medical device 200. In some embodiments, image sensors 110 may be configured to capture images when in a retracted state (e.g. during deployment of main sheath 235) so that robotic medical device 200 may be visually navigated through the patient's body (e.g. by a medical practitioner) to a location of interest.

Figure 2C:
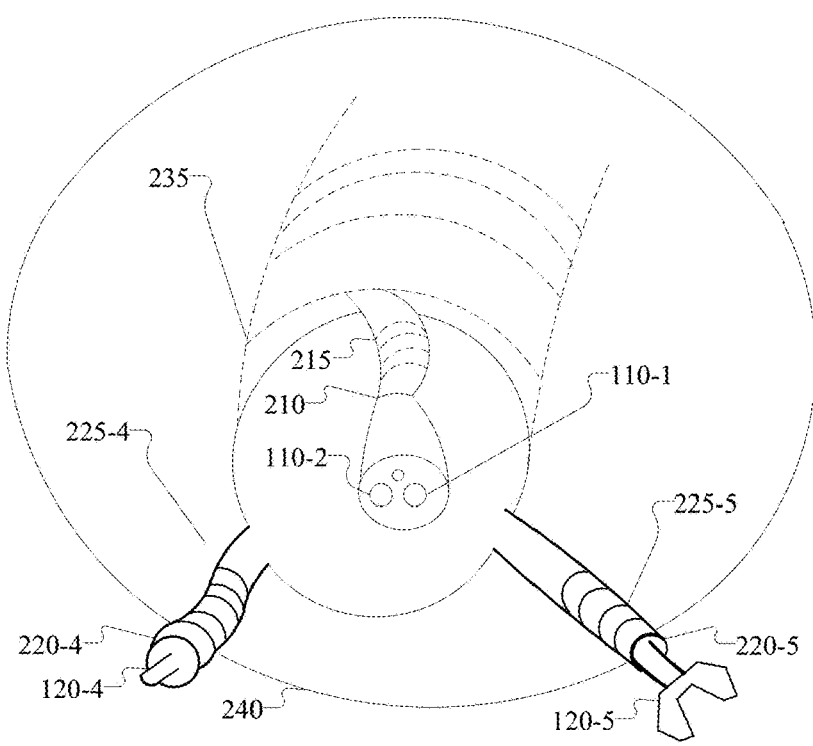
FIG. 2C shows the image sensor and instruments of the example robotic medical device of FIG. 2B in a deployed state.

FIG. 2C shows the image sensors 110, instrument 120-4 (shown as a cautery knife in FIG. 2B), and instrument 120-5 (shown as a grasper in FIG. 2B) each individually coupled to the corresponding distal ends (210, 220-3, and 220-4, respectively) of corresponding flexible articulating sub-arms 215, 225-4, and 225-5, respectively, in a deployed state in accordance with certain embodiments disclosed herein. For example, once a user has articulated and moved main sheath 235 through GI tract 240 to a location of interest, the user may select and deploy one or more sub-arms such as sub-arms 215, 225-4, and 225-5. For example, image sensors 110 may be moved and oriented to capture images of the location of interest (e.g. a colon polyp) and one or more of instruments 120-3 and/or 120-4 may be moved into positions to perform appropriate medical procedures.

As outlined above, in conventional devices, determining the positions of instruments 120 relative to the current FOV of image sensor 110 may be difficult and impose a cognitive load on the operator thereby detracting attention from the substantive procedures being performed. Further, the rigidity of the main sheath may limit the types of procedures that may be performed and/or increase procedural complications/risk.

In some embodiments, the user may configure robotic medical device 200 so that one or more instruments 120 may be automatically positioned within the current FOV upon user input (e.g. by activating a trigger on haptic interface 140 or some other means). In some embodiments, configuration information 177 (FIG. 1B) may indicate that some instruments 120 (e.g. cautery knife 120-4) are to be deactivated and/or disabled when outside the boundary of the current FOV to prevent accidental use and/or increase safety. In some embodiments, haptic interface 140 and visual interface 135 may be used to provide haptic feedback 141 and visual feedback 117, respectively, based on the position of one or more instruments 120 relative to the current FOV of image sensors 110 as described herein. The haptic feedback 141 and/or visual feedback 117 may facilitate maintenance of instrument position within the current FOV of image sensors 110 and/or returning instruments 120 to the FOV when the instruments 120 are outside the boundary of the current FOV.

Figure 3A:
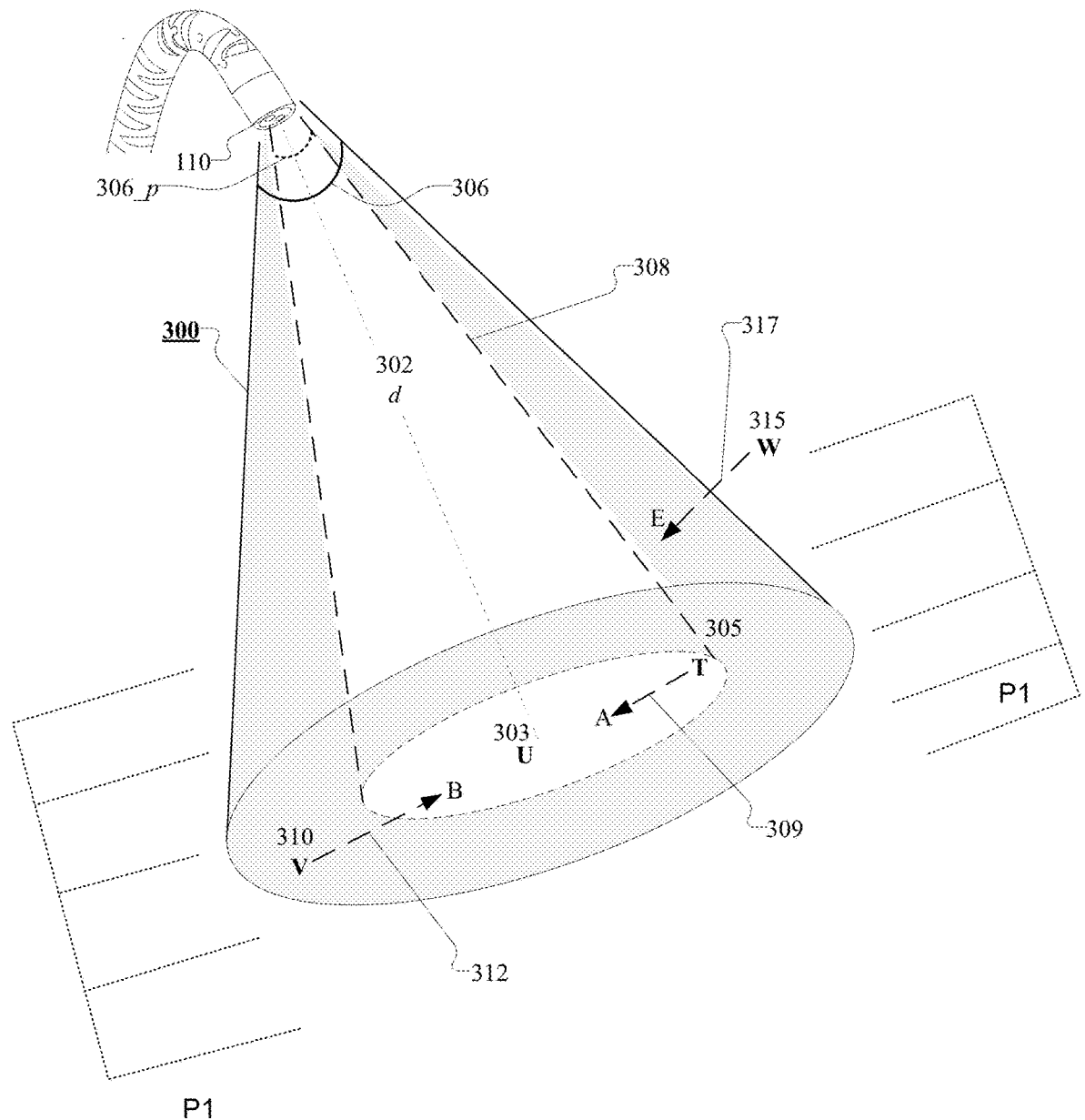
FIG. 3A shows an example FOV associated with an image sensor coupled to a robotic medical device illustrating potential locations of instruments relative to the current FOV.

FIG. 3A shows a FOV 300 associated with image sensors 110 coupled to a robotic medical device 200. FIG. 3A illustrates possible locations of instruments 120 (not shown in FIG. 3A) relative to the current FOV 300 of image sensors 110. FOV, as used herein, may also refer to an angle of coverage, which describes the angular range that the image sensor can effectively image. As outlined above, the FOV may be determined based on image sensor parameters (e.g. focal length, image sensor size). For example, FOV 300 may be specified or determined based on solid angle 306. The FOV associated with a pose may also be mathematically specified (e.g. based on a frame of reference such as an image sensor centric frame of reference).

FIG. 3A is merely an example to illustrate some scenarios referred to herein. As shown in FIG. 3A, an instrument (e.g. instrument 120-5) may be positioned at location T 305 or at location V 310 in current FOV 300. Further, Location T 305 may be within a first imaging volume 308 of current FOV 300. Locations within first imaging volume 308 of current FOV 300 are depicted by dashed lines in FIG. 3A. First imaging volume 308 may correspond to solid angle 306_p. For example, first imaging volume 308 may correspond to locations where imaging may be optimal and/or instruments 120 of robotic medical device 200 have satisfactory range of motion (e.g. based on the procedure being performed) and/or a lower likelihood of leaving current FOV 300 (e.g. when moved during the procedure). For example, configuration information 177 may include information related to first imaging volume 308 for various procedures and/or information to obtain first imaging volume 308. In some embodiments, first imaging volume 308 (e.g. which may correspond to locations where imaging may be optimal) may be procedure-specific and/or instrument specific to accommodate a range of instrument motion typical for the procedure and/or for the instrument thereby increasing the likelihood that the instrument remains in the FOV when performing the procedure.

FIG. 3A shows locations, such as point V 310, which may lie between current FOV 300 and first imaging volume 308. Thus, point V 310 may lie: (a) within current FOV 300, and (b) within a threshold of the boundary of current FOV 300 (e.g. outside of first imaging region 308). In some embodiments, the threshold may be a function of the depth d 302 from image sensor 110 to a plane (e.g. P1) perpendicular to the axis of current FOV 300 that includes the location (e.g. V 310), where the depth d 302 is measured in the direction of the axis of current FOV 300. For example, as described above, in embodiments with stereoscopic image sensors (or with depth sensors), depth information (e.g. depth d 302) may be present and/or determined from captured images 115. In FIG. 3A, locations between current FOV 300 and first imaging volume 308 (e.g. lying within a threshold of the boundary of current FOV 300) are indicated by the shaded area.

In some embodiments, when an instrument 120 is located at point T 305, the user may receive visual feedback 117 (e.g. on visual interface 135, which may be stereoscopic) indicative of direction TA 309 toward center U 303 (or an estimated center of the current FOV 300) or toward another point along the axis of current FOV 300. In some embodiments, the visual feedback 117 may comprise a directional indicator TU that may point in the direction of the shortest path toward center U 303 (e.g. along plane P1).

Figure 3B:
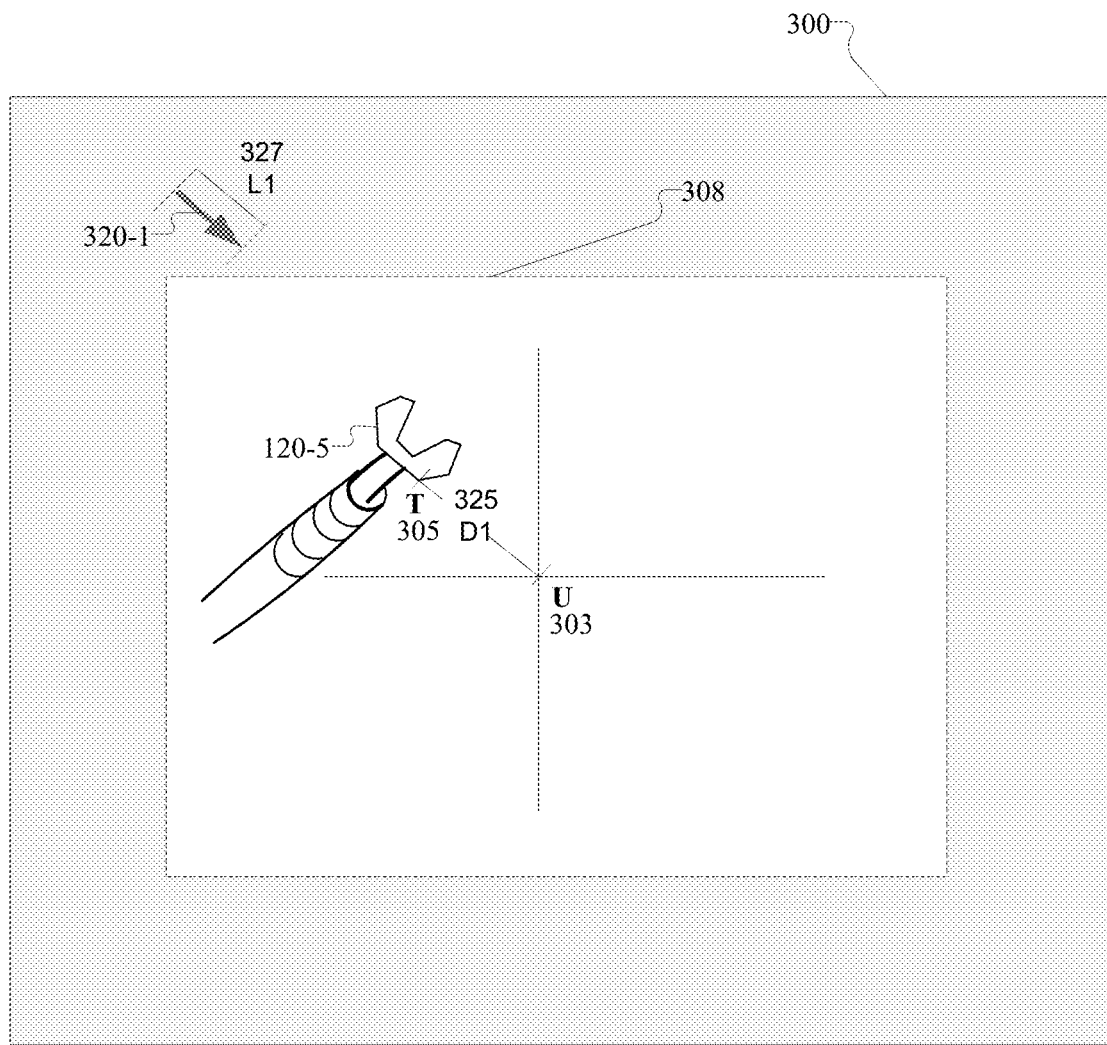
FIGS. 3B-3D show various potential locations of instruments relative to the FOV of the image sensor illustrating example visual feedback provided to a user based on the locations of the instruments relative to the current FOV.

Referring to FIG. 3B, instrument 120-5 is shown at location T 305 in current FOV 300. Location T 305 is within first imaging volume 308 (shown by dashed lines in FIG. 3B). FIG. 3B also shows example visual feedback 117 in the form directional indicator 320-1, where the length L1 327 of the directional indicator is proportional to the distance D1 325 between location T 305 and current FOV center U 303 (or a location estimated to be the center of current FOV 300). Further, directional indicator 320-1 may be oriented toward and point in the direction of TU.

Referring to FIG. 3A, in some embodiments, when an instrument 120 is located at point V 310, the user may receive visual feedback 117 (e.g. on visual interface 135) indicative of direction VB 312 toward center U 303 (or an estimated center of the current FOV 300) or toward another point along the axis of current FOV 300. In some embodiments, the visual feedback 117 may comprise a directional indicator VU that may point in the direction of the shortest path toward center U 303 (e.g. along plane P1).

Figure 3C:
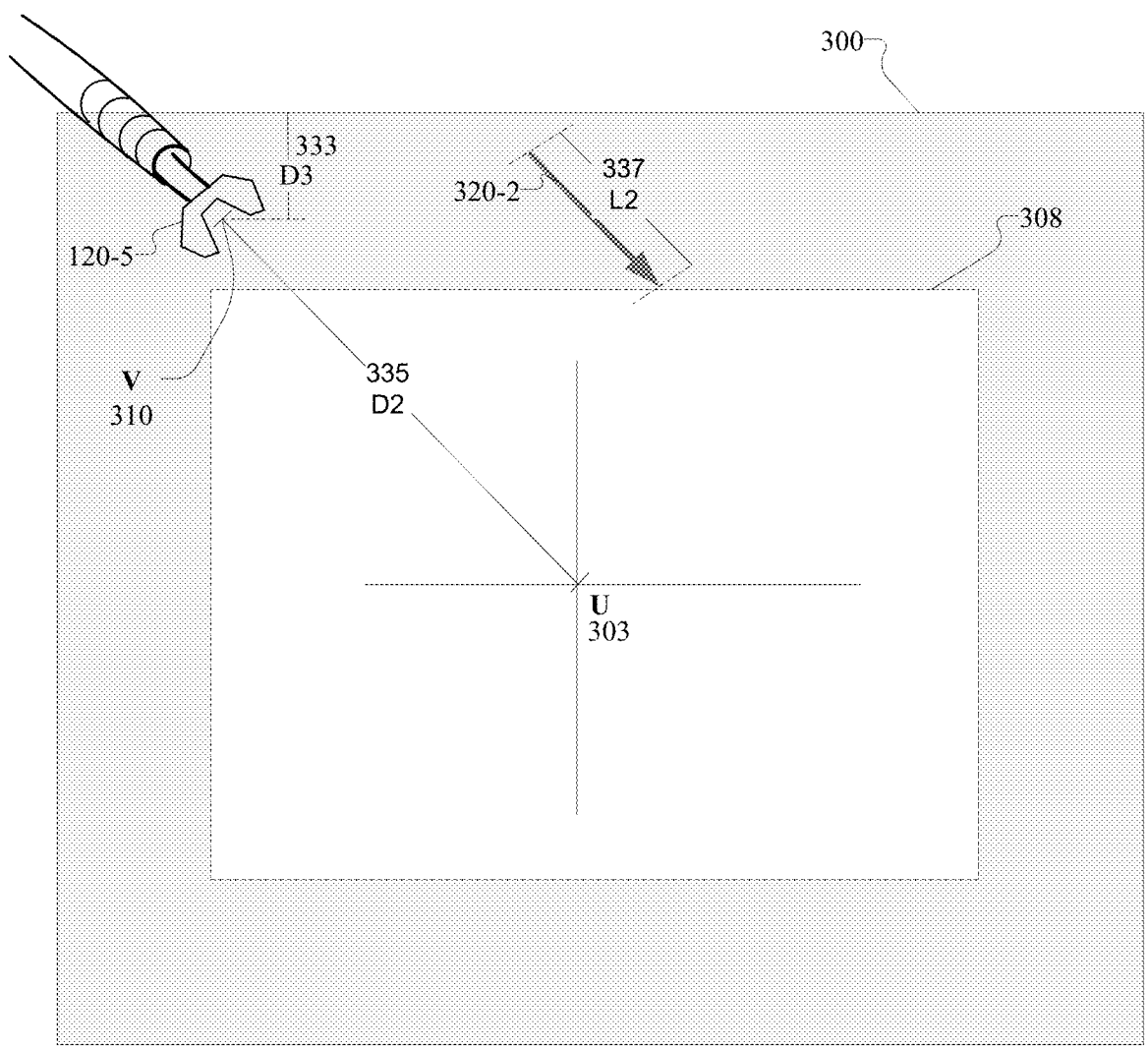

Referring to FIG. 3C, instrument 120-5 is shown at location V 310 in current FOV 300. Location V 310 is within current FOV 300 and within a threshold of a boundary of current FOV 300 (e.g. between current FOV 300 and first imaging volume 308 (shown by dashed lines in FIG. 3C). Specifically, instrument 120-5 is within current FOV 300 and at a distance D3 333 from the nearest boundary of FOV 300.

FIG. 3C also shows example visual feedback 117 in the form of directional indicator 320-2, where the length L2 337 of the directional indicator may be: (a) proportional to the distance D2 335 between location V 310 and current FOV center U 303 (or a location estimated to be the center of current FOV 300); or (b) inversely proportional to distance (e.g. D3 333) to the nearest boundary of current FOV 300. Further, directional indicator 320-2 may be oriented toward and point in the direction of VU. As shown in FIG. 3C, instrument 120-5 may be at a distance D3 333 from the nearest boundary of current FOV 300. In some embodiments, the visual feedback 117 may include progressively changing the color of directional indicator 320-2 (e.g. from green to yellow to orange to red) as the instrument is moved toward the boundary of current FOV 300 and/or other visual feedback 117 such as blinking the visual indicator, In the example above, when the instrument is outside current FOV 300 (or partially outside current FOV 300) the color of visual indicator 320-2 may be changed to red.

Referring to FIG. 3A, in some embodiments, when an instrument (e.g. instrument 120-5) is within current FOV 300 and within a threshold of the boundary of current FOV 300, (in addition to visual feedback 117 or instead of visual feedback 117) the user may receive haptic feedback 141. For example, if the instrument (e.g. instrument 120-5) is moved from point V 310 in a direction toward the boundary of current FOV 300 (e.g. in a direction away from the axis of current FOV 300 or away from center U 303), the haptic feedback 141 may comprise haptic resistance (e.g. to the movement of haptic interfaces 140). For example, the haptic resistance provided may be inversely proportional to the distance D3 333 (FIG. 3C) of the instrument (e.g. instrument 120-5) from the nearest boundary of current FOV 300. Thus, a user may encounter greater haptic feedback 141 (e.g. haptic resistance to movement) as the instrument (e.g. instrument 120-5) approaches the boundary of current FOV 300.

In some embodiments, when an instrument (e.g. instrument 120-5) is located at point W 315 outside of the boundary of current FOV 300, the user may receive visual feedback 117 (e.g. on visual interface 135) indicative of direction WE 317 toward current FOV 300. In some embodiments, the visual feedback 117 may comprise a directional indicator that may point in the direction of the shortest path to bring the instrument into current FOV 300. In some embodiments, the directional indication may be colored red to indicate that current location W 315 is outside FOV 300. In some embodiments, the user may be able to provide input (e.g. via user interface 130) to indicate that automatic repositioning of one or more instruments 120 into current FOV 300 is desired. In response, robotic medical system 100 may reposition instruments 120 that are currently outside the boundary of current FOV 300, to a location within current FOV 300. In some embodiments, control model 175 may be used to determine that one or more instruments 120 are outside current FOV 300. In some embodiments, input provided by sensors (e.g. electromagnetic sensors and/or other sensors) may be used, at least in part, to determine the locations of instruments 120 that are outside current FOV 300. In some embodiments, instruments 120 deemed as, or configured to be, preferably operated with user supervision may not be moved automatically (and/or visual feedback 117 may be provided to indicate that one or more instruments 120 have not been moved or cannot be moved automatically).

Figure 3D:
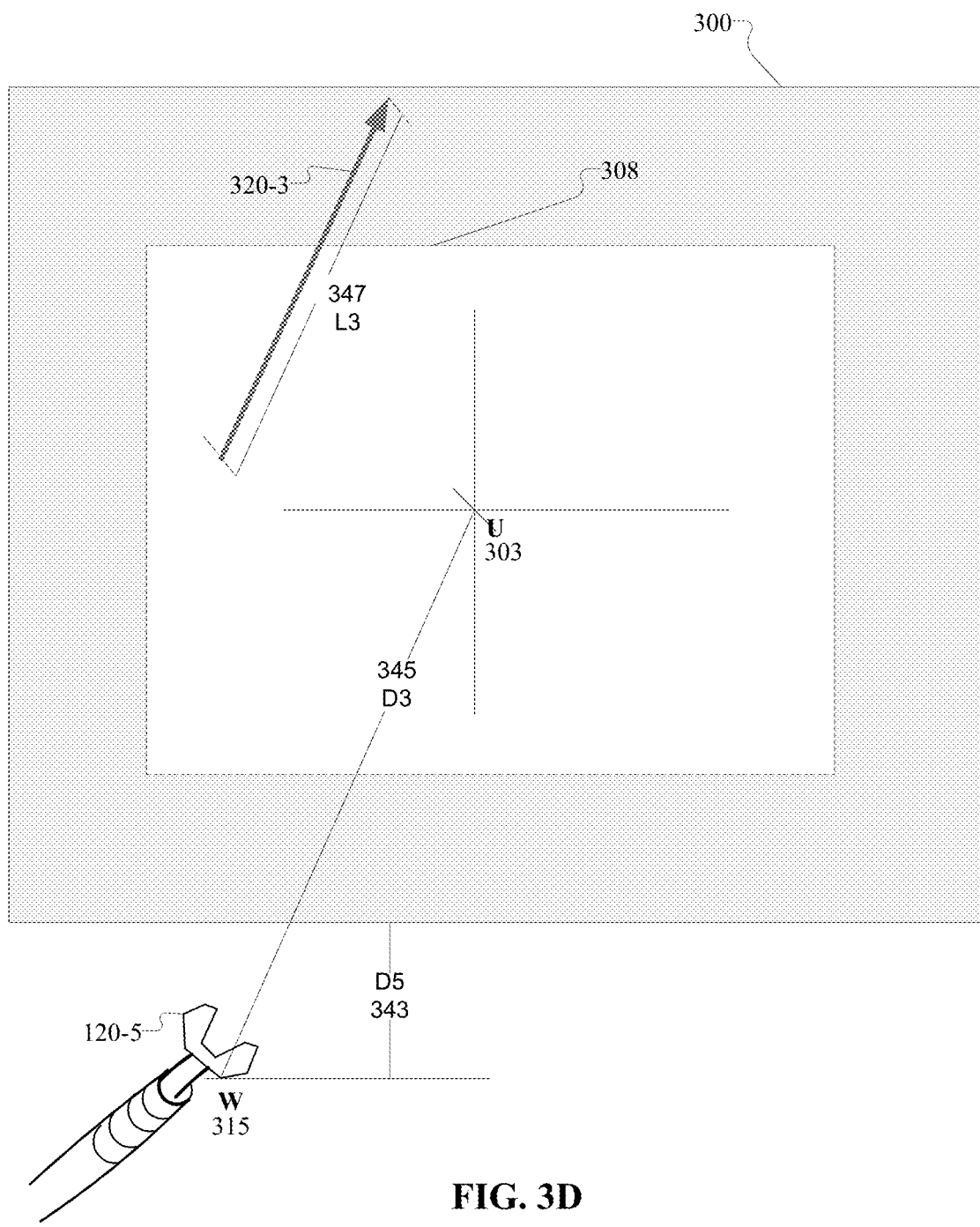

Referring to FIG. 3D, instrument 120-5 is shown at location W 315 in current FOV 300. Location W 315 is outside the boundary of current FOV 300. Specifically, instrument 120-5 is outside current FOV 300 and at a distance D5 343 from the nearest boundary of current FOV 300.

FIG. 3D also shows example visual feedback 117 in the form of directional indicator 320-3, where the length L3 347 of the directional indicator 320-3 is proportional to the distance D4 345 between location W 315 and FOV center U 303 (or a location estimated to be the center of current FOV 300). Thus, in the examples above, in relation to the lengths L1 327, L2 337, and L3 347 of the directional indicators L1<L2<L3 (because D1<D2<D3).

Further, directional indicator 320-3 may be oriented toward and point in the direction of WU. As shown in FIG. 3D, instrument 120-5 may be at a distance D5 343 from the nearest boundary of current FOV 300. In some embodiments, the visual feedback 117 may include blinking a visual indicator and/or changing the color of the visual indicator 320-3 to red when the instrument is outside current FOV 300 (or partially outside current FOV 300).

Referring to FIG. 3A, in some embodiments, when an instrument is outside the boundary of current FOV 300 (in addition to visual feedback 117 or instead of visual feedback 117) the user may receive haptic feedback 141. For example, if the instrument is moved from point W 315 in a direction away from the boundary of current FOV 300 (e.g. in a direction away from the axis of current FOV 300 or away from center U 303), the haptic feedback 141 may comprise haptic resistance (e.g. to the movement of haptic interfaces 140). For example, the haptic resistance provided may be proportional to the distance D4 345 (FIG. 3D) of the instrument (e.g. instrument 120-5) from the nearest boundary of current FOV 300. Thus, a user may encounter greater haptic feedback 141 (e.g. haptic resistance to movement) as the instrument (e.g. instrument 120-5) is moved further away from the boundary of current FOV 300.

In some embodiments, the haptic resistance to movement further away from the boundary of current FOV 300 may be greater when instrument 120-5 is outside the boundary, relative to haptic resistance to movement toward the boundary when instrument 120-5 is within the boundary of current FOV 300. In some embodiments, the haptic resistance and/or visual indicators may be adjusted dynamically. For example, as the user moves toward the center of current FOV 300, the haptic resistance may decrease dynamically based on the distance from the current location of instrument 120-5 to the center of current FOV 300. Similarly, the length and color of the directional indicators may change as instrument 120-5 is moved closer to the center of current FOV 300. For example, the length of the directional indicator may be decreased and the color changed from red to amber to green based on its current location. Conversely, as instrument 120-5 is moved in a direction away from the center of current FOV 300, the length of the directional indicators may be dynamically increased and/or haptic resistance to movement of instrument 120-5 may be dynamically increased based on a current location of instrument 120-5 relative to FOV 300. Further, the color of the directional indicator may be changed from green to amber to red as instrument 120-5 moves from a location within imaging volume 308 (green) to a location between imaging volume 308 and FOV 300 (amber), to a location outside FOV 300 (red).

Figure 4A:
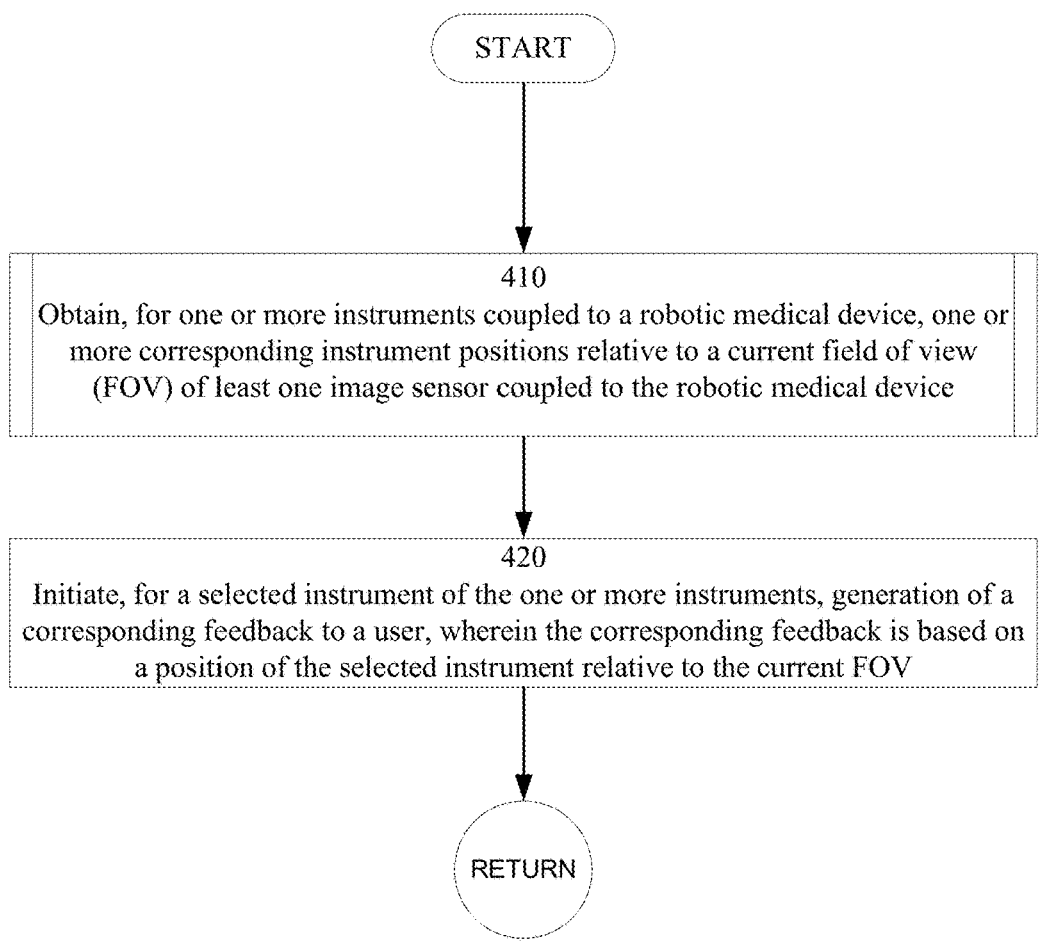
FIGS. 4A and 4B show a flowchart of example method to provide user feedback based on the locations of the instruments relative to the current FOV of an image sensor coupled to a robotic medical device.
Figure 4B:
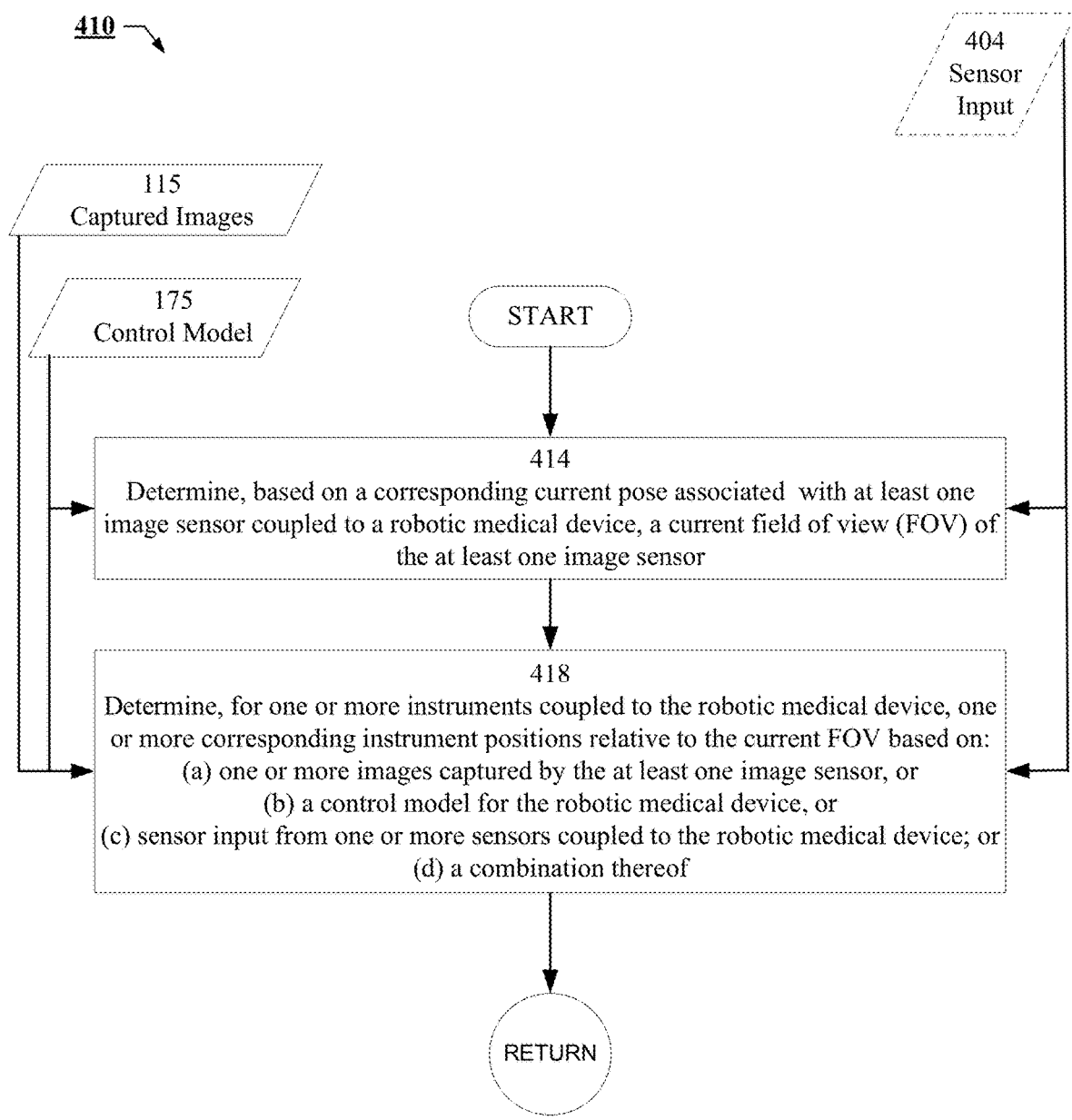

FIGS. 4A and 4B shows an exemplary flowchart related to a method 400 of facilitating user feedback based on the locations of instruments (e.g. instruments 120) relative to a current FOV 300 of at least one image sensor (e.g. image sensors 110) coupled to a robotic medical device (e.g. robotic medical device 200). In some embodiments, some or all of method 400 may be implemented by one or more of: robotic medical system 100, user interface 130, robotic medical device control system 160, and/or processor(s) 150.

In some embodiments, user interface 130 may comprise processor(s) 150, which may be coupled to robotic medical device 200. Although shown separately in FIG. 1A, in some embodiments, robotic medical device control system 160 may comprise user interface 130 and processor(s) 150, which may be coupled to robotic medical device 200. The coupling of processor(s) 150 to robotic medical device 200 may be communicative (e.g. using wired or wireless communication to exchange information and commands), and/or electrical and/or or electronic, and/or electromagnetic, and/or electro-mechanical, and/or some combination of the above. For example, processor(s) 150 may interact electronically with image sensors 110 to control the capture of images and/or receive captured images. In some embodiments, processor(s) 150 and/or robotic medical device control system 160 may use one or more of electrical, electronic, electromagnetic, and/or electro-mechanical couplings to monitor and obtain sensor input, and/or to initiate the driving robotic medical device 200 and/or to control actuators that articulate and move main sheath 235, sub-arms, image sensors 110, instruments 120, and/or haptic interface 140.

In some embodiments, processor(s) 150 may be distributed between robotic medical device control system 160 and user interface 130. For example, user interface 130 may be located remotely from robotic medical device control system 160 and/or robotic medical device 200, and exchange information (e.g. one or more of: captured images 115, and/or sensor/actuator information 167, and/or instrument state 165) and commands with robotic medical device 200 and/or robotic medical device control system 160 and some or all of method 400 may be performed by user interface 130 based on the received information. In situations where there is an increased danger of risk to medical practitioners or patients (e.g. from infectious/contagious diseases etc.) user interface 130 communicatively coupled (e.g. via wired communications interface 107 and/or wireless communication interface 105) to robotic medical device 200 that forms part of robotic medical system 100 may be used at some specified distance or through barriers (e.g. such as optically transparent but biologically protective barriers) to perform medical procedures on the patient while maintaining safety and distancing protocols.

Further, in situations when skilled practitioners are unavailable (e.g. in remote locations), user interface 130 communicatively coupled (e.g. via wired communications interface 107 and/or wireless communication interface 105) to robotic medical device 200 that forms part of robotic medical system 100 may be used telesurgically (e.g. via wired communications interface 107 or wireless communication interfaces 105) to perform or guide performance of medical procedures (e.g. using locally available resources). For example, local medical practitioner(s) may monitor and supervise patient condition and/or the procedure being performed in accordance with any local regulations and/or safety protocols. In the example above, a medical facility deploying robotic medical device 200 may be able to use a remote first medical practitioner (e.g. at a remote first medical facility) for one medical procedure using a first user interface 130-1 (e.g. telesurgically), and use a second medical practitioner (e.g. at a remote second medical facility) for another medical procedure using a second user interface 130-2 telesurgically.

As another embodiment, an integrated robotic unit, which may include processor(s) 150, UI 130, robotic medical device control system 160, and robotic medical device 200, and may perform method 400. For example, in the integrated robotic unit, information and commands may be exchanged with robotic medical device 200 using wired communication and robotic medical device 200 may be monitored, controlled, and driven using electrical, electronic, and/or electro-mechanical techniques.

In block 410, for one or more instruments 120 coupled to a robotic medical device, 200 one or more corresponding instrument positions relative to a current FOV 300 of least one image sensor 110 coupled to the robotic medical device may be obtained. As one example, user interface 130 may receive (e.g. from processor(s) 150 and/or robotic medical device control system 160) the corresponding instrument positions 119 of one or more instruments 120 relative to current pose and/or relative to FOV 300 of the at least one image sensor 110.

In some embodiments, referring to FIG. 4B, in block 414, the current FOV (e.g. current FOV 300) of at least one image sensor 110 may be obtained based on a corresponding current pose associated with at least one image sensor 110, which may be coupled to robotic medical system 100.

In some embodiments, user interface 130 and/or a processor(s) 150 and/or robotic medical device control system 160 may determine the corresponding instrument positions 119 of one or more instruments 120 relative to current pose and/or FOV 300 of the at least one image sensor 110. For example, input from control model 175 may be used, at least in part, to determine the pose of the at least one image sensor 110 and/or the current FOV 300. In some embodiments, the pose of the at least one image sensor 110 may be determined based, in part, on optional sensor input 404 (e.g. provided by one or more sensors coupled to robotic medical device 200). The optional sensor input may comprise input from electromagnetic sensors and/or electro-mechanical sensors (e.g. coupled to robotic medical device 200), which may facilitate determination of articulation and motion of main sheath 235, image sensors 110 and image sensor sub-arm 215, and/or instruments 120-$i$ and corresponding instrument sub-arms 220. If the total number of instruments 120 coupled to robotic medical device 200 is M, then the set of instruments may be written as I={120-$i$|1≤$i$≤M}. In some embodiments, sensor actuator information 167 may comprise sensor input 404 to method 400.

In some embodiments, the optional sensor input 404 may further include input from 3D shape sensing fiber optic sensors, fiber optic force and/or pressure sensors such as photonic crystal fiber (PCF) sensors or Fiber Bragg Grating (FBG) sensors, or make use of scattering arising from FBG sensors or inherently present, or make use of post-process produced Rayleigh scattering.

In block 418, for one or more instruments 120 coupled to the robotic medical device 200, one or more corresponding instrument positions relative to the current FOV 300 may be determined based on: (a) one or more captured images 115, which may be captured by the at least one image sensor 110, or (b) a control model 175 for the robotic medical device 200, or (c) optional sensor input 404 from one or more sensors coupled to the robotic medical device 200; or (d) some combination of (a)-(c) above.

For example, the corresponding positions of one or more instruments relative to the current FOV 300 may be determined based, at least in part, on captured images 115 (e.g. captured by the at least one image sensor 110), when the corresponding positions of the one or more instruments 120 lie within the current FOV 300 and the one or more instruments 120 are visible in the captured images 115. In some embodiments, input from control model 175 may be used, at least in part, to determine the corresponding positions of the one or more instruments 120 relative to the current FOV 300. In some embodiments, the position of the instrument 120 may be determined based in part on optional sensor input 404 from one or more sensors coupled to the robotic medical system 100, or a combination of captured images 115 and sensor input 404.

Referring to FIG. 4A, in block 420, the generation of a corresponding feedback for a selected instrument 120-$k$, 1≤$k$≤M, of the one or more instruments 120 in I may be initiated, wherein the corresponding feedback may be based on a position of the selected instrument 120-$k$ relative to the current FOV 300. The feedback corresponding to the selected instrument 120-$k$ may be provided to a user (e.g. via user interface 130). In some embodiments, the feedback corresponding to the selected instrument 120-$k$ may comprise one or more of: corresponding haptic feedback 141-$k$; or corresponding visual feedback 117-$k$; or a combination of visual feedback 117-$k$ and haptic feedback 141-$k$. In some embodiments, haptic feedback may be provided using haptic interface 140 (FIG. 1B) and visual feedback may be provided using visual interface 135 (FIG. 1B).

In some embodiments, initiating generation the corresponding haptic feedback 141-$k$ may comprise initiating generation of a corresponding haptic resistance to a movement-related input for the selected instrument 120-$k$ in response to a determination that: (a) the position of the selected instrument 120-$k$ is within the current FOV 300 and within a threshold of the current FOV 300 (e.g. between first imaging volume 308 and FOV 300 in FIG. 3A) and the movement-related input is indicative of movement of the selected instrument 120-$k$ toward a boundary of the current FOV 300, or (b) the position of the selected instrument 120-$k$ is outside the boundary (e.g. outside FOV 300) and the movement-related input is indicative of movement of the selected instrument 120-$k$ further away from the boundary.

In some embodiments, the corresponding haptic resistance to movement of the selected instrument 120-$k$ may be inversely proportional to the distance between the boundary and the position of the selected instrument 120-$k$ when the position of the instrument 120-$k$ is within the current FOV 300 and within the threshold of the boundary (e.g. between first imaging volume 308 and FOV 300 in FIG. 3A). In some embodiments, the corresponding haptic resistance to movement of the selected instrument 120-$k$ may be proportional to the distance between the boundary of current FOV 300 and the position of the selected instrument 120-$k$ when the position of the selected instrument 120-$k$ is outside the boundary. In some embodiments, the corresponding haptic resistance to movement of the instrument 120-$k$ may be lower when the position of the selected instrument 120-$k$ is within the boundary of the current FOV 300 relative to the corresponding haptic resistance when the position of the selected instrument 120-$k$ is outside the boundary.

In some embodiments, initiating generation of the corresponding visual feedback 117 may comprise displaying a corresponding directional indicator 320-$k$ indicating a movement direction for the selected instrument 120-$k$ to bring the selected instrument 120-$k$ (a) further into the current FOV 300 in response to a determination that the position of the selected instrument 120-$k$ is within the current FOV 300 and within a threshold of a boundary of the current FOV 300 (e.g. between first imaging volume 308 and FOV 300 in FIG. 3A), or (b) into the current FOV 300 in response to a determination that the position of the selected instrument 120-$k$ is outside the boundary of the current FOV 300. In some embodiments, a magnitude of the directional indicator (e.g. length of the corresponding directional indicator) 320-$k$ may be proportional to the distance between the position of the selected instrument 120-$k$ and a specified location (e.g. a center of current FOV 300 or a point on a central axis of FOV 300, or another location in first imaging volume 308) within the current FOV 300

In some embodiments, method 400 may further comprise (e.g. after block 420 or block 430) selectively disabling functionality associated with the selected instrument 120-$k$, when the instrument 120-$k$ is outside the current FOV 300. For example, the selected instrument 120-$k$ (e.g. cautery knife 120-4, for k=4) may be deactivated and/or disabled (or configured to be deactivated or disabled) when outside the boundary of the current FOV 300 to prevent accidental use, inadvertent contact with tissue, and/or to increase safety.

In some embodiments, method 400 may comprise (e.g. after block 420 or block 430) automatically moving the selected instrument 120-$k$ into a position within the current FOV 300 in response to user input when the position of the selected instrument 120-$k$ is outside a boundary of the current FOV 300.

Figure 5:
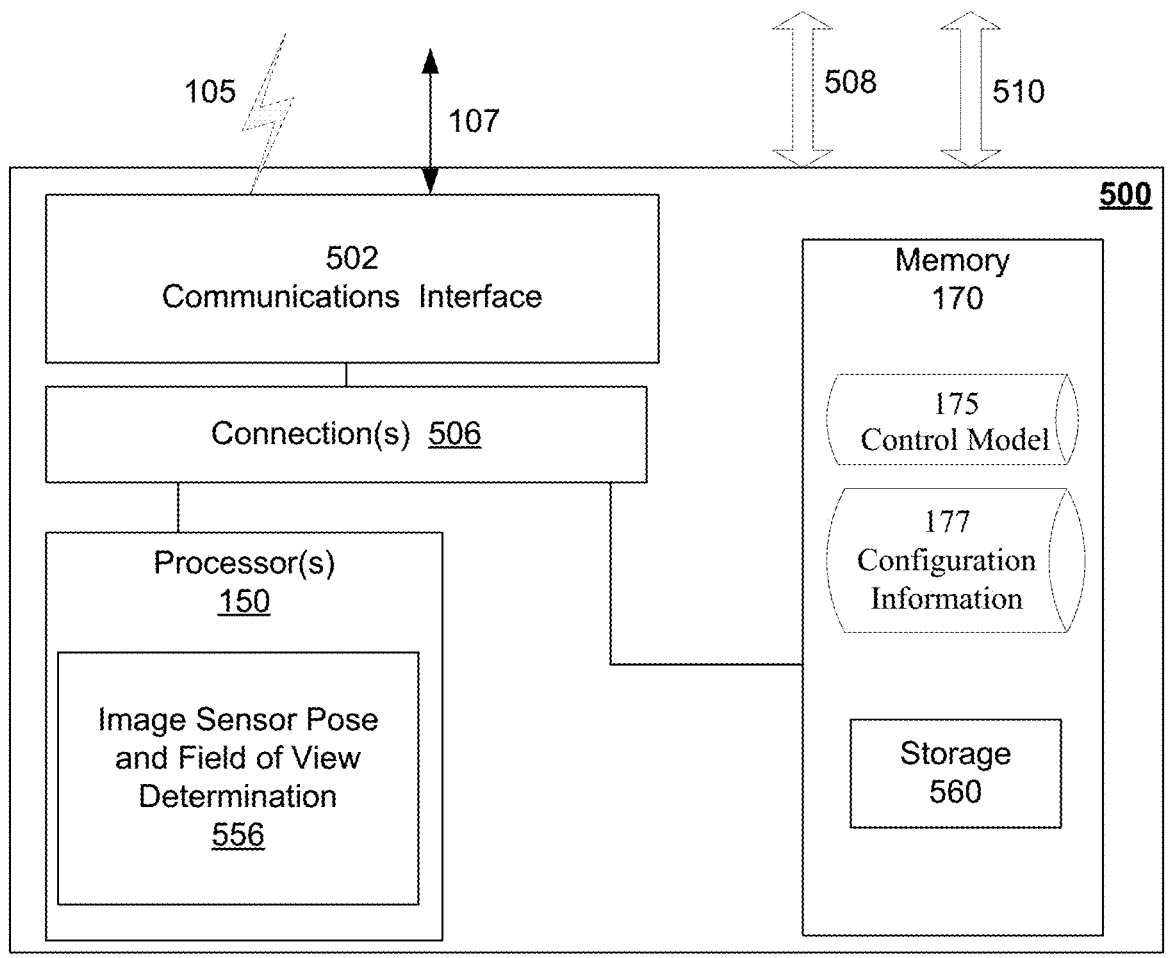
FIG. 5 shows an exemplary computing subsystem to facilitate instrument visualization.

FIG. 5 shows an exemplary computing subsystem 500 to facilitate instrument visualization. Computing subsystem 500 may form part of robotic medical system 100, and/or robotic medical device 200, and/or another robotic device and facilitate instrument visualization. For example, computing subsystem 500 may be part of robotic medical system 100. In some embodiments, computing subsystem 500 form part of user interface 130 and/or robotic medical device control system 160, and/or and may be coupled to robotic medical device 200. In some embodiments, computing subsystem 500 may perform some or all of methods shown in FIGS. 4A and 4B.

As shown in FIG. 5, computing subsystem 500 may include processor(s) 150, memory 170, and communications interface 502, which may be connected to each other using connections 506. Connections 506 may take the form of buses, lines, fibers, electronic interfaces, links, etc., which may operationally couple the above components.

Communications interface 502 may be capable of wired (e.g. using wired communications interface 107) or wireless (e.g. using wireless communication interface 105) communications with another device (e.g. robotic medical device control system 160, user interface 130, and/or robotic medical device 200). Captured images 115, instrument state 165, sensor/actuator information 167, etc., may be received over communications interface 502. User input may also be transmitted (e.g. when computing subsystem is part of user interface 130) or received (e.g. when computing subsystem forms part of robotic medical device control system 160) using communications interface 502. In some embodiments, communications interface 502 may be used to receive, transmit, or relay signals related to user feedback (haptic and/or visual to appropriate components of robotic medical system 100). Wireless communication may include communication over Wireless Personal Area Networks (WPANs), which may be based on the IEEE 802.15x standards, Wireless Local Area Networks (WLANs), which may be based on the IEEE 802.11 standards, and/or over Wireless Wide Area Networks (WWAN), which may be based on cellular communication standards such as a Fifth Generation (5G) network, or Long Term Evolution (LTE).

Computing subsystem 500 may also include control interface 508, which may provide control input (e.g. activate, select, deploy, deactivate, retract, etc.) and command input to drive robotic medical device 200 (e.g. main sheath 235, sub-arms, image sensors 110, and/or instruments 120). In some embodiments, control interface 508 may also output haptic feedback 141 (e.g. based on the position of instrument 120 relative to current FOV 300 of image sensors 110 and user input related to instrument movement direction). Control interface 508 may communicate with processor(s) 150 and may be controlled by processor(s) 150.

Computing subsystem 500 may also include display interface 510, which may interact with a display (e.g. a 3D or stereoscopic display) to provide visual feedback 117 (e.g. based on the position of instrument 120 relative to current FOV 300 of image sensors 110). For example, display interface may generate graphics, and/or other visualization, which may augment or overlay the captured images. In some embodiments, display interface 510 may be used to generate visual feedback 117 to display directional indicator 320 indicating a corresponding movement direction to bring one or more instruments 120 further into the current FOV 300. Display interface 510 may communicate with processor(s) 150 and may be controlled by processor(s) 150.

In some embodiments, memory 170 may comprise main or primary memory (e.g. RAM) and storage 560. Program code may be stored in memory 170, and read and executed by processor(s) 150 to perform the techniques disclosed herein. Storage 560 may include ROM, EPROM, NVRAM, flash memory, secondary storage, and other computer readable media (e.g. fixed and/or removable drives, optical disks, etc.). Computer-readable media may be encoded with databases, data structures, etc. and/or with computer programs. By way of example, and not limitation, such computer-readable media may also include CD-ROM, memory cards, portable drives, or other optical disk storage, magnetic disk storage, solid state drives, other storage devices, or any other medium that can be used to store desired program code in the form of instructions and/or data structures and that can be accessed by a computer.

In some embodiments, images captured by image sensors 110, instrument state 165, sensor/actuator information 167, motion control/instrument control input 162, and other information pertaining to robotic medical device 200 may be stored in memory 170 for operational, training, logging, and other purposes. For example, based on user input and configuration information 177, a procedure performed by robotic medical device 200 may be recorded and replayed/analyzed at a subsequent time. As another example, the procedure may be live streamed via communications interface 502 (e.g. to local and/or remote medical practitioners during telesurgery, and/or for educational or training purposes).

Memory 170 may include control model 175, which may be used by processor(s) 150 to determine the positions of instruments 120 relative to image sensors 110. In some embodiments, control model 175 may include calibrated instrument control models, which may be used to estimate an instrument position (e.g. relative to image sensors 110) based on one or more of: motion control/instrument control input 162, configuration information 177, and/or motion-related user input 143. In some embodiments, control model 175 may also use information from one or more sensors (when present) in robotic medical device 200.

Memory 170 may include configuration information 177, which may provide information pertaining to the instruments on robotic medical device 200, image sensor configuration (e.g. lens focal length and other parameters), user preferences (e.g. sensitivity to user movement, the desired level of haptic feedback 141, automatic maintenance of FOV over instruments 120, indicating whether functionality of one or more instruments 120 is to be disabled when not in the FOV of image sensors 110, display parameters, etc.) and/or an operational configuration or mode of operation of robotic medical system 100.

The methodologies described herein may be implemented in hardware, firmware, software, or any combination thereof. For a hardware implementation, the processor(s) 150 may be implemented within one or more application specific integrated circuits (ASICs), digital signal processors (DSPs), image processors, digital signal processing devices (DSPDs), programmable logic devices (PLDs), field programmable gate arrays (FPGAs), processors, controllers, micro-controllers, microprocessors, electronic devices, other electronic units designed to perform the functions described herein, or any combination thereof. In some embodiments, processor(s) 150 may include capabilities to: determine a current pose of image sensor 110 based on sensor input, determine a FOV associated with image sensors 110 determine a FOV 300 for image sensors 110 based on a current pose, process images, determine and track corresponding positions of instruments 120 relative to a current image sensor FOV 300, provide input to control haptic feedback 141, provide visual feedback 117, and provide input to control actuators on robotic medical device 200. Processor(s) 150 may also include functionality perform other well-known computer vision and image processing functions such as feature extraction from images, image comparison, image matching, object recognition and tracking, image compression and decompression, etc.

For example, captured images 115 may be processed using object recognition and/or tracking techniques by processor(s) 150 to determine a location of one or more instruments 120 in the current FOV 300 of image sensor 110. In some embodiments, based on configuration information 177 (e.g. as set or invoked by a user), processor(s) 150 may use object tracking techniques to keep an instrument in the current FOV 300 of image sensors 110 during a procedure (or portion of a procedure). For example, the location of instrument 120 may be tracked over a sequence of captured images 115. Object tracking techniques may use one or more of: control model 175 (which may receive input from sensors coupled to or associated instruments 120), the known instrument form factor (e.g. grasper, cauterizing knife, etc.), markers on instruments to facilitate object recognition, identification, and tracking, and/or other instrument characteristics. Object tracking techniques may be used in conjunction with image processing and computer vision techniques and sensor input to locate an instrument in an image. Processor(s) 150 may then initiate the movement of image sensors 110 to keep the instrument 120 in the FOV of image sensors 110. When instruments are visible, because the form factors of instruments coupled to robotic medical device 200 are known, object recognition and tracking techniques may be applied to identify visible instruments in a sequence of image(s) captured by image sensors 110 and determine their respective locations relative to the image sensors and/or the corresponding image sensor FOV. When instruments 120 are not currently visible, sensor input along with prior known instrument positions may be used by control model 175 to determine instrument positions at a current time.

Although the present disclosure is described in connection with specific embodiments for instructional purposes, the disclosure is not limited thereto. Various adaptations and modifications may be made to the disclosure without departing from the scope. Therefore, the spirit and scope of the appended claims should not be limited to the foregoing description.

What is claimed is:

1. A processor-implemented method comprising:
   (a) obtaining, for one or more instruments coupled to a robotic medical device, one or more corresponding instrument positions and instrument movement directions relative to a current field of view (FOV) of at least one image sensor coupled to the robotic medical device; and
   (b) initiating, for a selected instrument of the one or more instruments, generation of a corresponding feedback to a user, wherein the corresponding feedback is in real-time and is based on an obtained position of the selected instrument relative to the current FOV, wherein the corresponding feedback includes a directional indicator indicating the corresponding instrument movement directions,
   wherein the corresponding feedback comprises a corresponding visual feedback,
   wherein initiating generation of the corresponding visual feedback comprises:
   initiating display of the directional indicator indicating a movement direction for the selected instrument to bring the selected instrument:
   (i) further into the current FOV in response to a determination that the obtained position of the selected instrument is within the current FOV and within a threshold of a boundary of the current FOV, or
   (ii) into the current FOV in response to a determination that the obtained position of the selected instrument is outside the boundary of the current FOV.

2. The method of claim 1, wherein obtaining the one or more corresponding instrument positions relative to the current FOV comprises:
   (i) determining, based on a corresponding current pose associated with the at least one image sensor, the current FOV of the at least one image sensor; and
   (ii) determining, for the one or more instruments, the one or more corresponding instrument positions relative to the current FOV based on:
   (A) one or more images captured by the at least one image sensor,
   (B) a control model for the robotic medical device,
   (C) sensor input from one or more sensors coupled to the robotic medical device, or
   (D) a combination thereof.

3. The method of claim 2, wherein the one or more sensors comprise:
   (i) electromagnetic sensors,
   (ii) electro-mechanical sensors, wherein the electro-mechanical sensors comprise micro electro-mechanical sensors (MEMS),
   (iii) 3D shape sensing fiber optic sensors,
   (iv) fiber optic force sensors,
   (v) fiber optic pressure sensors, wherein the fiber optic force sensors and the fiber optic pressure sensors comprise one or more of:

photonic crystal fiber (PCF) sensors or Fiber Bragg Grating (FBG) sensors, or (vi) a combination thereof.

4. The method of claim 1, wherein the corresponding feedback further comprises a corresponding haptic feedback.

5. The method of claim 4, wherein initiating generation of the corresponding haptic feedback comprises:
initiating generation of a corresponding haptic resistance to a corresponding movement-related user input for a movement of the selected instrument in response to a determination that:
(i) the obtained position of the selected instrument is within the current FOV and within a threshold of the current FOV and the corresponding movement-related user input indicates the movement of the selected instrument is toward a boundary of the current FOV, or
(ii) the obtained position of the selected instrument is outside the boundary and the corresponding movement-related user input indicates the movement of the selected instrument is further away from the boundary.

6. The method of claim 5, wherein:
the corresponding haptic resistance is inversely proportional to a distance between the boundary and the obtained position of the selected instrument when the obtained position of the selected instrument is within the current FOV and within the threshold of the boundary; and
the corresponding haptic resistance is proportional to the distance between the boundary and the obtained position of the selected instrument when the obtained position of the selected instrument is outside the boundary.

7. The method of claim 6, wherein the corresponding haptic resistance is lower when the obtained position of the selected instrument is within the boundary of the current FOV relative to the corresponding haptic resistance when the obtained position of the selected instrument is outside the boundary.

8. The method of claim 1, wherein initiating display of the directional indicator is to bring the selected instrument further into the current FOV in response to the determination that the obtained position of the selected instrument is within the current FOV and within the threshold of a boundary of the current FOV.

9. The method of claim 1, wherein a magnitude of the directional indicator is:
proportional to a distance between the obtained position of the selected instrument and a specified location within the current FOV.

10. The method of claim 1, further comprising:
automatically disabling a functionality associated with the selected instrument, when the selected instrument is outside a boundary of the current FOV.

11. The method of claim 1, further comprising:
initiating automatic movement of the selected instrument into a position within the current FOV, in response to a user input, when the obtained position of the selected instrument is outside a boundary of the current FOV.

12. A robotic medical device comprising:
(a) at least one image sensor;
(b) one or more instruments; and
(c) a processor communicatively coupled to the at least one image sensor and the one or more instruments, wherein the processor is configured to:
(i) obtain, for the one or more instruments, one or more corresponding instrument positions and instrument movement directions that are based in part on a current image of the one or more instruments captured by the at least one image sensor, the at least one image sensor having a current field of view (FOV), and
(ii) initiate, for a selected instrument of the one or more instruments, generation of a corresponding feedback to a user, wherein the corresponding feedback is based on a prior position of the selected instrument relative to the current FOV, wherein the corresponding feedback includes a directional indicator indicating the corresponding instrument movement directions,
wherein the corresponding feedback comprises a corresponding visual feedback,
wherein to initiate generation of the corresponding visual feedback, the processor is configured to:
initiate display of a corresponding directional indicator indicating a movement direction for the selected instrument to bring the selected instrument:
(i) further into the current FOV in response to a determination that the prior position of the selected instrument is within the current FOV and within a threshold of a boundary of the current FOV, or
(ii) into the current FOV in response to a determination that the prior position of the selected instrument is outside the boundary of the current FOV.

13. The robotic medical device of claim 12, further comprising:
one or more sensors coupled to the processor, wherein to obtain the one or more corresponding instrument positions based in part on the current FOV of the at least one image sensor, the processor is further configured to:
(i) determine, based on a corresponding current pose associated with the at least one image sensor, a current FOV of the at least one image sensor, and
(ii) determine the one or more corresponding instrument positions relative to the current FOV based on:
(A) one or more images captured by the at least one image sensor,
(B) a control model for the robotic medical device,
(C) sensor input from the one or more sensors, or
(D) a combination thereof.

14. The robotic medical device of claim 13, wherein the one or more sensors comprise:
(i) electromagnetic sensors,
(ii) electro-mechanical sensors, wherein the electro-mechanical sensors comprise micro electro-mechanical sensors (MEMS),
(iii) 3D shape sensing fiber optic sensors,
(iv) fiber optic force sensors,
(v) fiber optic pressure sensors, wherein the fiber optic force sensors and the fiber optic pressure sensors comprise one or more of:
photonic crystal fiber (PCF) sensors or Fiber Bragg Grating (FBG) sensors, or
(vi) a combination thereof.

15. The robotic medical device of claim 12, wherein the corresponding feedback further comprises a corresponding haptic feedback.

16. The robotic medical device of claim 15, wherein to initiate generation of the corresponding haptic feedback, the processor is configured to:

initiate generation of a corresponding haptic resistance to a corresponding movement-related user input for a movement of the selected instrument in response to a determination that:
  (i) the prior position of the selected instrument is within the current FOV and within a threshold of the current FOV and the movement-related user input indicates that the selected instrument is to be moved toward a boundary of the current FOV, or
  (ii) the prior position of the selected instrument is outside the boundary and the movement-related user input indicates that the selected instrument is to be moved further away from the boundary.

17. A processor-implemented method comprising:
(a) obtaining, for one or more instruments coupled to a robotic medical device, one or more corresponding instrument positions and instrument movement directions relative to a current field of view (FOV) of at least one image sensor coupled to the robotic medical device; and
(b) initiating, for a selected instrument of the one or more instruments, generation of a corresponding feedback to a user, wherein the corresponding feedback is in real-time and is based on an obtained position of the selected instrument relative to the current FOV, wherein the corresponding feedback includes a directional indicator indicating the corresponding instrument movement directions,
wherein the corresponding feedback comprises a corresponding haptic feedback,
wherein initiating generation of the corresponding haptic feedback comprises:
  initiating generation of a corresponding haptic resistance to a corresponding movement-related user input for a movement of the selected instrument in response to a determination that:
    (i) the obtained position of the selected instrument is within the current FOV and within a threshold of the current FOV and the corresponding movement-related user input indicates the movement of the selected instrument is toward a boundary of the current FOV, or
    (ii) the obtained position of the selected instrument is outside the boundary and the corresponding movement-related user input indicates the movement of the selected instrument is further away from the boundary.

18. The method of claim 17, wherein initiating generation of the corresponding haptic resistance is in response to a determination that: the obtained position of the selected instrument is within the current FOV and within a threshold of the current FOV and the corresponding movement-related user input indicates the movement of the selected instrument is toward a boundary of the current FOV.

19. The method of claim 17, wherein initiating generation of the corresponding haptic resistance is in response to a determination that: the obtained position of the selected instrument is outside the boundary and the corresponding movement-related user input indicates the movement of the selected instrument is further away from the boundary.

* * * * *